(12) United States Patent
Beaton et al.

(10) Patent No.: US 10,752,607 B2
(45) Date of Patent: Aug. 25, 2020

(54) POLYMORPHS OF N-[(6-CYANO-2-FLUORO)-3-METHOXYPHENYL)METHYL]-3-(METHOXYMETHYL)-1-({4-[(2-OXOPYRIDIN-1-YL)METHYL]PHENYL}METHYL)PYRAZOLE-4-CARBOXAMIDE AS KALLIKREIN INHIBITORS

(71) Applicant: KALVISTA PHARMACEUTICALS LIMITED, Wiltshire (GB)

(72) Inventors: Haydn Beaton, Loughborough (GB); Jonathan Yates Boxhall, Loughborough (GB); David Malcolm Crowe, Reading (GB)

(73) Assignee: KALVISTA PHARMACEUTICALS LIMITED, Porton Down, Wiltshire (GB)

( * ) Notice: Subject to any disclaimer, the term of this patent is extended or adjusted under 35 U.S.C. 154(b) by 0 days.

(21) Appl. No.: 16/303,350

(22) PCT Filed: Jun. 1, 2017

(86) PCT No.: PCT/GB2017/051575
§ 371 (c)(1),
(2) Date: Nov. 20, 2018

(87) PCT Pub. No.: WO2017/208002
PCT Pub. Date: Dec. 7, 2017

(65) Prior Publication Data
US 2019/0169162 A1 Jun. 6, 2019

Related U.S. Application Data

(60) Provisional application No. 62/344,133, filed on Jun. 1, 2016.

(30) Foreign Application Priority Data

Jun. 1, 2016 (GB) .................................. 1609603.4

(51) Int. Cl.
*C07D 401/10* (2006.01)
*A61P 27/02* (2006.01)
*A61K 9/00* (2006.01)

(52) U.S. Cl.
CPC .......... *C07D 401/10* (2013.01); *A61K 9/0053* (2013.01); *A61P 27/02* (2018.01); *A61K 2121/00* (2013.01); *C07B 2200/13* (2013.01)

(58) Field of Classification Search
CPC ...... C07D 401/10; A61P 27/02; A61K 9/0053
(Continued)

(56) References Cited

U.S. PATENT DOCUMENTS 5,187,157 A    2/1993   Kettner et al.
7,101,878 B1   9/2006   Anderson et al.
(Continued)

FOREIGN PATENT DOCUMENTS

EA    201200917    12/2012
EP    1426364 A1   6/2004
(Continued)

OTHER PUBLICATIONS

European Patent Office Communication in Application 17728612.7, dated Apr. 1, 2020, 5 pages. (Year: 2020).*

(Continued)

*Primary Examiner* — Daniel R Carcanague
(74) *Attorney, Agent, or Firm* — BakerHostetler

(57) ABSTRACT

The invention provides new polymorphs of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, pharmaceutical compositions containing them and their use in therapy.

(Continued)

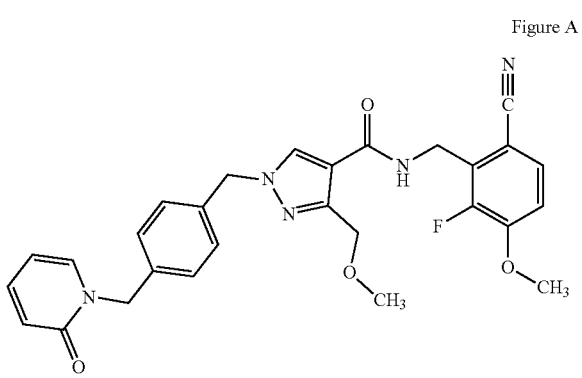

Figure A

37 Claims, 7 Drawing Sheets

Figure 1:
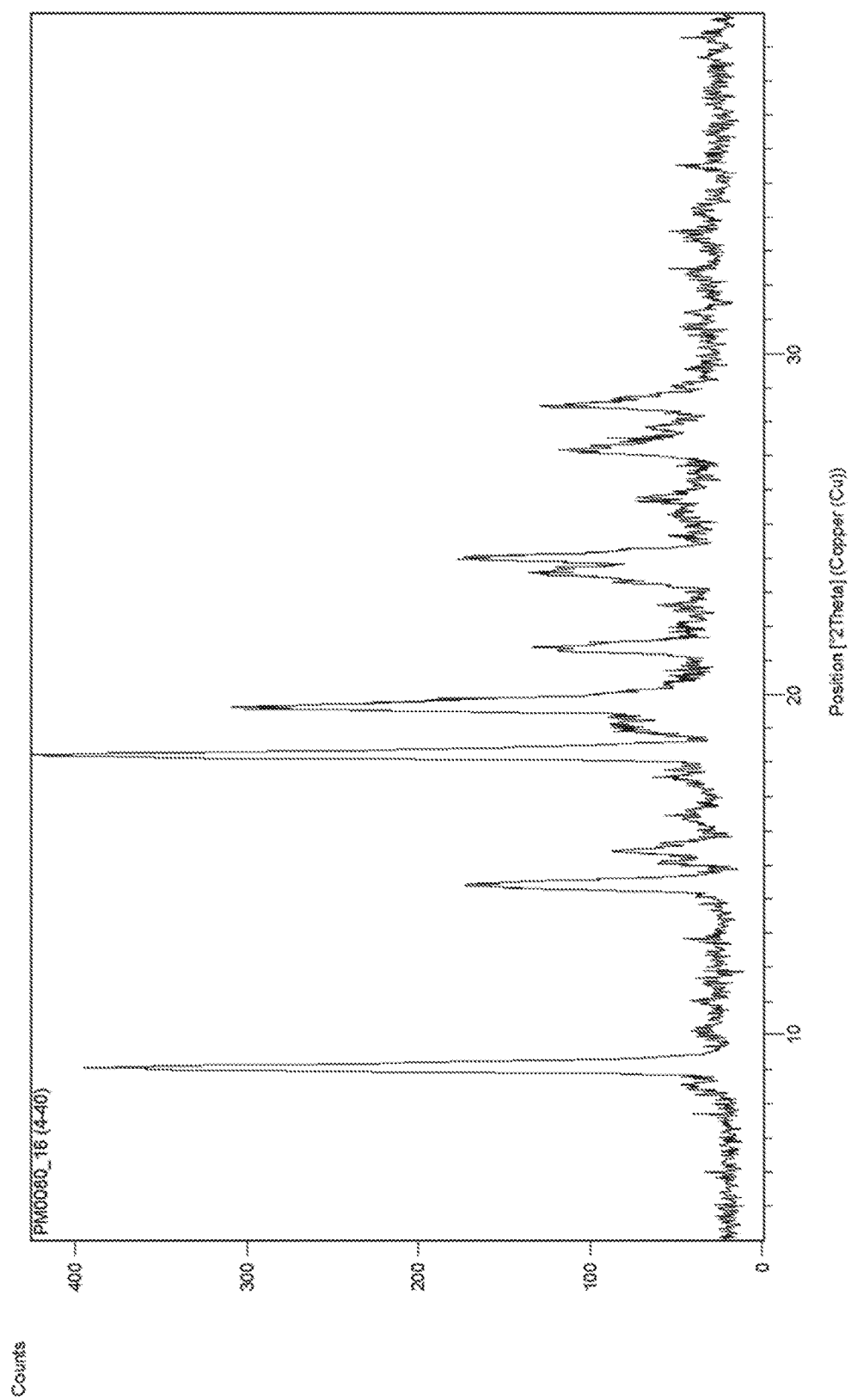

(58) Field of Classification Search
USPC .................................................. 546/243
See application file for complete search history.

(56) References Cited

U.S. PATENT DOCUMENTS

| | | | |
|---|---|---|---|
| 8,207,378 B2 | 6/2012 | Steinmetzer et al. | |
| 9,382,219 B2 | 7/2016 | Das et al. | |
| 9,512,065 B2 * | 12/2016 | Northen | C07C 237/22 |
| 9,533,987 B2 * | 1/2017 | Davie | C07D 403/14 |
| 9,670,157 B2 * | 6/2017 | Allan | C07D 401/14 |
| 9,738,641 B2 * | 8/2017 | Edwards | C07D 401/04 |
| 10,221,161 B2 * | 3/2019 | Edwards | C07D 401/14 |
| 2007/0254894 A1 | 11/2007 | Kane et al. | |
| 2008/0221091 A1 | 9/2008 | Gege et al. | |
| 2009/0163545 A1 | 6/2009 | Goldfarb | |
| 2010/0113782 A1 | 5/2010 | Bolin et al. | |
| 2011/0152533 A1 | 6/2011 | Sinha et al. | |
| 2012/0298326 A1 | 11/2012 | Born | |
| 2014/0213611 A1 * | 7/2014 | Evans | C07C 237/22 |
| | | | 514/311 |
| 2014/0378474 A1 | 12/2014 | Flohr et al. | |
| 2015/0191421 A1 * | 7/2015 | Northen | C07C 237/22 |
| | | | 514/616 |
| 2015/0315198 A1 | 11/2015 | Li et al. | |
| 2017/0305863 A1 * | 10/2017 | Evans | C07D 401/14 |
| 2018/0319782 A1 * | 11/2018 | Davie | C07D 401/14 |

FOREIGN PATENT DOCUMENTS

| | | |
|---|---|---|
| EP | 1568698 A1 | 8/2005 |
| EP | 2281885 A1 | 2/2011 |
| JP | 2010-520294 A | 6/2010 |
| RU | 2485114 C2 | 6/2013 |
| WO | WO 1992/004371 | 3/1992 |
| WO | WO 1994/029335 | 12/1994 |
| WO | WO 1995/007921 | 3/1995 |
| WO | 03/35076 A1 | 5/2003 |
| WO | 03/37274 A2 | 5/2003 |
| WO | WO 2003/076458 | 9/2003 |
| WO | 03/91226 A1 | 11/2003 |
| WO | 2004/062657 A1 | 7/2004 |
| WO | 2004/069792 A2 | 8/2004 |
| WO | 2005/049578 A1 | 6/2005 |
| WO | 2005/079800 A1 | 9/2005 |
| WO | WO 2005/123680 | 12/2005 |
| WO | WO 2006/091459 | 8/2006 |
| WO | 2006/114313 A1 | 11/2006 |
| WO | 2007/011626 A2 | 1/2007 |
| WO | 2007/113289 A1 | 10/2007 |
| WO | WO 2008/016883 | 2/2008 |
| WO | WO 2008/049595 | 5/2008 |
| WO | WO 2008/091692 | 7/2008 |
| WO | 2008/121670 A1 | 10/2008 |
| WO | 2009/012998 A1 | 1/2009 |
| WO | 2009/026407 A1 | 2/2009 |
| WO | 2009/083553 A1 | 7/2009 |
| WO | WO 2009/097141 | 8/2009 |
| WO | 2009/106980 A2 | 9/2009 |
| WO | 2009/114677 A1 | 9/2009 |
| WO | WO 2010/142801 | 12/2010 |
| WO | 2011/075684 A1 | 6/2011 |
| WO | 2011/094496 A2 | 8/2011 |
| WO | WO 2011/118672 | 9/2011 |
| WO | 2012/009009 A2 | 1/2012 |
| WO | WO 2012/004678 | 1/2012 |
| WO | WO 2012/017020 | 2/2012 |
| WO | 2012/142308 A1 | 10/2012 |
| WO | 2012/174362 A1 | 12/2012 |
| WO | 2013/005045 A1 | 1/2013 |
| WO | 2013/048982 A1 | 4/2013 |
| WO | 2013/049096 A1 | 4/2013 |
| WO | 2013/120104 A2 | 8/2013 |
| WO | WO 2013/111107 | 8/2013 |
| WO | WO 2013/111108 | 8/2013 |
| WO | 2013/130603 A1 | 9/2013 |
| WO | 2014/006414 A1 | 1/2014 |
| WO | 2014/108406 A1 | 7/2014 |
| WO | 2014/108685 A1 | 7/2014 |
| WO | WO 2014/108679 A1 | 7/2014 |
| WO | 2014/145986 A1 | 9/2014 |
| WO | WO 2014/188211 A1 | 11/2014 |
| WO | WO 2015/022546 | 2/2015 |
| WO | WO 2015/022547 | 2/2015 |
| WO | WO 2015/103317 | 7/2015 |
| WO | WO 2015/134998 | 9/2015 |
| WO | WO 2015/171526 | 11/2015 |
| WO | WO 2015/171527 | 11/2015 |
| WO | WO 2016/011209 | 1/2016 |
| WO | WO 2016/029214 | 2/2016 |
| WO | 2016/044662 A1 | 3/2016 |
| WO | WO 2016/083816 | 6/2016 |
| WO | WO 2016/083818 | 6/2016 |
| WO | WO 2016/083820 | 6/2016 |
| WO | 2016/138532 A1 | 9/2016 |
| WO | 2017/001924 | 1/2017 |
| WO | WO 2017/001926 | 1/2017 |
| WO | WO 2017/001936 | 1/2017 |
| WO | WO 2017/072020 | 5/2017 |
| WO | WO 2017/072021 | 5/2017 |
| WO | 2017/207986 A1 | 12/2017 |
| WO | 2017/207989 A1 | 12/2017 |
| WO | WO-2017207983 A1 * | 12/2017 ........... C07D 401/14 |
| WO | WO-2017207985 A1 * | 12/2017 ........... C07D 401/10 |
| WO | WO-2017208005 A1 * | 12/2017 ........... C07D 401/10 |
| WO | WO 2018/011628 | 1/2018 |
| WO | WO2019106359 A1 * | 6/2019 ........... C07D 401/14 |
| WO | WO2019106375 A1 * | 6/2019 ........... C07D 401/14 |
| WO | WO2019106377 A1 * | 6/2019 ........... C07D 401/14 |

OTHER PUBLICATIONS

Babu et al., "A Simple, Sensitive and Selective Fluorogenic Assay to Monitor Plasma Kallikrein Inhibitory Activity of BCX4161 in Activated Plasma", Journal of Allergy and Clinical Immunology, 133(2), Supplement Feb. 2014, p. AB40.
Bhoola et al., "Bioregulation of Kinins: Kallikreins, Kininogens and Kininases", Pharmacological Rev., 1992, 44(1), 80 pages.
Bhoola et al., "Kallikrein-Kinin Cascade", Encyclopedia of Respiratory Medicine, 2006; 483-493.
Bird et al., "Effects of plasma kallikrein deficiency on haemostasis and thrombosis in mice: murine ortholog of the Fletcher trait," Thrombosis and Haemostasis, 2012, 107, 1141-50.
Björkqvist et al., "Plasma kallikrein: the bradykinin-producing enzyme," Thrombosis and Haemostasis, 2013, 110, 399-407.
Bryant et al., "Human plasma kallikrein-kinin system: physiological and biochemical parameters" Cardiovascular and haematological agents in Medicinal Chemistry, 7, 2009, 234-250.

(56) References Cited

OTHER PUBLICATIONS

Campbell, "Towards understanding the kallikrein-kinin system: insights from the measurement of kinin peptides", Brazilian Journal of Medical and Biological Research, 2000, 33, 665-677.
Chilcote et al., "ASP-634: An Oral Drug Candidate for Diabetic Macular Edema", ARVO 2012 May 6-May 8, 2012, Fort Lauderdale, Florida, Presentation 2240.
Clermont et al., "Plasma kallikrein mediates retinal vascular dysfunction and induces retinal thickening in diabetic rats", Diabetes, May 2011, 60(5), 1590-1598.
Collis et al, "BCX4161, an Oral Kallikrein Inhibitor: Safety and Pharmacokinetic Results of a Phase 1 Study in Healthy Volunteers", Journall of Allergy and Clinical Immunology, 133(2), Supplement, Feb. 2014, p. AB39.
Elman et al., "Randomized trial evaluating ranibizumab plus prompt or deferred laser or triamcinolone plus prompt laser for diabetic macular edema", Ophthalmology, Apr. 27, 2010.
Evans et al., "Selective Inhibitors of Plasma Kallikrein", Immunopharmacology, May 1996, 32(1-3), 115-116.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.
Griesbacher et al., "Involvement of tissue kallikrein but not plasma kallikrein in the development of symptoms mediated by endogenous kinins in acute pancreatitis in rats" British Journal of Pharmacology 137, 2002, 692-700.
Johansen et al., "Assay of Kallikrein Inhibitors and Levels of Acetone-Activated Kallikrein in Plasma Specimens from Reactors to Dextran or to Contrast Media", International Journal Tissue Reactions, 1986, 8, 185-192.
Katsuura et al., "Effects of a highly selective synthetic inhibitor of plasma kallikrein on disseminated intravascular coagulation in rats," Thrombosis Research, 1996, 82, 361-368.
Kolte et al. "Biochemical characterization of a novel high-affinity and specific kallikrein inhibitor", British Journal of Pharmacology, 2011, 162(7), 1639-1649.
Lehmann, "Ecallantide (DX-88), a plasma kallikrein inhibitor for the treatment of hereditary angioedema and the prevention of blood loss in on-pump cardiothoracic surgery", Expert Opinion Biol. Ther., Jul. 2008, 8(8), 1187-1199.
Liang et al. "Fast-Dissolving Intraoral Drug Delivery Systems", Expert Opinion in Therapeutic Patents, 2001, 11(6), 981-986.
Lieberman et al., Pharmaceutical Dosage Forms: Tablets, Second Edition, vol. 2, XP008099925; 15 pages (front page and list of contents included), 145-157, (1990).
Lieberman et al., Pharmaceutical Dosage Forms Tablets, Second Edition, vol. 1, 1980; (front page and list of contents included) 6 pages.
Liu et al., "Hyperglycemia-induced cerebral hematoma expansion is mediated by plasma kallikrein," Nat. Med., 2011, 17, 206-210.
Marceau et al., "Bradykinin Receptor Ligands: Therapeutic Perspectives", Nature Reviews Drug Discovery, Oct. 2004, 3, 845-852.
Okada et al., "Development of potent and selective plasmin and plasma kallikrein inhibitors and studies on the structure-activity relationship", Chem. Pharm. Bull., 2000, 48, 1964-1972.
Remington's Pharmaceutical Sciences, Remington: Practice of the Science and Pharmacy; 19th Edition, Mack Publishing Company, 1995; 5 pages.
Revenko et al., "Selective depletion of plasma prekallikrein or coagulation factor XII inhibits thrombosis in mice without increased risk of bleeding," Blood, 2011, 118, 5302-5311.
Shori et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), 1209-1217.
Sturzebecher et al., "Inhibition of Human Mast Cell Tryptase by Benzamicline Derivatives", Biological Chemistry Hoppe-Seyler, Oct. 1992, 373(2), 1025-1030.
Sturzebecher et al., "Novel Plasma Kallikrein Inhibitors of the Benzarnidine Type", Brazilian J. Med. Biol. Res, 1994, 27, 1929-1934.
Tanaka et al., "Evaluation of a novel kallikrein inhibitor on hemostatic activation in vitro," Thrombosis Research, 2004, 113, 333-339.
Teno et al., "Development of Active Center-Directed Plasmin and Plasma Kallikrein Inhibitors and Studies on the Structure-Inhibitory Activity Relationship", Chemical and Pharmaceutical Bulletin, 1993, 41(6), 1079-1090.
Young et al. "Small molecule inhibitors of plasma kallikrein" Bioorg. Med Chem. Letts. 16, 2006, 2034-2036.
Chang et al., "Discovery of highly potent small molecule kallikrein inhibitors" Medicinal Chemistry 2, 545-553, (2006).
Registry No. 1580327-09-8, Chemical Library—FCH Group, Apr. 4, 2014, 1 page.
Registry No. 1575214-30-0, Chemical Library—FCG Group, Mar. 28, 2014, 1 page.
Registry No. 1573976-69-8, Chemical Library—FCG Group, Mar. 26, 2014, 1 page.
Registry No. 1572946-10-I, Chemical Library—FCG Group, Mar. 25, 2014, 1 page.
Registry No. 1572436-72-6, Chemical Library—FCG Group, Mar. 24, 2014, 1 page.
Registry No. 1570266-44-2, Chemical Library—FCG Group, Mar. 19, 2014, 1 page.
Registry No. 1569406-35-4, Chemical Library—FCG Group, Mar. 18, 2014, 1 page.
Registry No. 1386189-59-8, Chemical Library—FCG Group, Aug. 3, 2012, 1 page.
Registry No. 1320653-15-3, Chemical Library—FCG Group, Aug. 21, 2011, 1 page.
Registry No. 1318167-86-0, Chemical Library—FCG Group, Aug. 15, 2011, 1 page.
Registry No. 1171693-25-6, Chemical Library—FCG Group, Aug. 2, 2009, 1 page.
Registry No. 1094996-93-6, Chemical Library—FCG Group, Jan. 22, 2009, 1 page.
Registry No. 1086603-52-2, Chemical Library—FCG Group, Dec. 18, 2008, 1 page.
Registry No. 1086603-42-0, Chemical Library—FCG Group, Dec. 18, 2008, 1 page.
Registry No. 1086603-37-3, Chemical Library—FCG Group, Dec. 18, 2008, 1 page.
Registry No. 1280842-43-4, Chemical Library—FCG Group, Apr. 18, 2011, 1 page.
Registry No. 1278351-92-0, Chemical Library—FCG Group, Apr. 11, 2011, 1 page.
Registry No. 1625594-62-8, Chemical Library—FCG Group, Sep. 24, 2014, 1 page.
Registry No. 1575116-26-5, Chemical Library—FCG Group, Mar. 28, 2014, 1 page.
Registry No. 1390613-03-2, Chemical Library—FCG Group, Aug. 13, 2012, 1 page.
Registry No. 1321521-84-9, Chemical Library—FCG Group, Aug. 12, 2011, 1 page.
Registry No. 1321195-15-6, Chemical Library—FCG Group, Aug. 21, 2011, 1 page.
Registry No. 1318604-27-1, Chemical Library—FCG Group, Aug. 16, 2011, 1 page.
Registry No. 1317855-54-1, Chemical Library—FCG Group, Aug. 15, 2011, 1 page.
Registry No. 1317328-27-0, Chemical Library—FCG Group, Aug. 14, 2011, 1 page.
Registry No. 1171669-07-0, Chemical Library—FCG Group, Aug. 02, 2009, 1 page.
Registry No. 1170030-40-6, Chemical Library—FCG Group, Jul. 29, 2009, 1 page.
Registry No. 1103271-51-7, Chemical Library—FCG Group, Feb. 9, 2009, 1 page.
Registry No. 1062408-24-5, Chemical Library—FCG Group, Oct. 17, 2008, 1 page.

(56) References Cited

OTHER PUBLICATIONS

Registry No. 1061709-51-0, Chemical Library—FCG Group, Oct. 15, 2008, 1 page.
Registry No. 1028361-95-6, Chemical Library—FCG Group, Jun. 16, 2008, 1 page.
Registry No. 1028096-34-5, Chemical Library—FCG Group, Jun. 13, 2008, 1 page.
Registry No. 1028094-50-9, Chemical Library—FCG Group, Jun. 13, 2008, 1 page.
Registry No. 1028093-96-0, Chemical Library—FCG Group, Jun. 13, 2008, 1 page.
Registry No. 1027627-81-1, Chemical Library—FCG Group, Jun. 12, 2008, 1 page.
Registry No. 1015534-45-8, Chemical Library—FCG Group, Apr. 18, 2008, 1 page.
Registry No. 956747-39-0, Chemical Library—FCG Group, Dec. 5, 2007, 1 page.
Registry No. 956529-72-9, Chemical Library—FCG Group, Dec. 3, 2007, 1 page.
Registry No. 956521-49-6, Chemical Library—FCG Group, Dec. 3, 2007, 1 page.
Registry No. 956444-80-7, Chemical Library—FCG Group, Dec. 2, 2007, 1 page.
Registry No. 956290-77-0, Chemical Library—FCG Group, Nov. 29, 2007, 1 page.
Registry No. 956190-38-8, Chemical Library—FCG Group, Nov. 28, 2007, 1 page.
Registry No. 955899-78-2, Chemical Library—FCG Group, Nov. 25, 2007, 1 page.
Registry No. 955867-36-4, Chemical Library—FCG Group, Nov. 23, 2007, 1 page.
Registry No. 879300-81-9, Chemical Library—FCG Group, Apr. 5, 2006, 1 page.
Registry No. 879195-72-9, Chemical Library—FCG Group, Apr. 4, 2006, 1 page.
PubChem Compound 40150888 May 30, 2009.
PubChem Compound 51143945 May 3, 2011.
PubChem Compound 52011740 May 20, 201t.
PubChem Compound 52011741 May 20, 200t.
PubChem Compound 52011742 May 20, 201t.
PubChem Compound 52011935 May 20, 201t.
PubChem Compound 52011936 May 20, 201t.
PubChem Compound 52011937 May 20, 201t.
PubChem Compound 52011938 May 20, 201t.
PubChem Compound 55389827 Jan. 25, 2012.
PubChem Compound 55408484 Jan. 25, 2012.
PubChem Compound 55408530 Jan. 25, 2012.
PubChem Compound 55408677 Jan. 25, 2012.
PubChem Compound 55408742 Jan. 25, 2012.
PubChem Compound 55408894 Jan. 25, 2012.
PubChem Compound 55438190 Jan. 25, 2012.
PubChem Compound 55494217 Jan. 25, 2012.
PubChem Compound 55650494 Jan. 25, 2012.
PubChem Compound 60376550 Oct. 18, 2012.
PubChem Compound Id 22830339 Dec. 5, 2007.
PubChem Compound Id 24488625 Feb. 29, 2008.
PubChem Compound Id 38284485 May 29, 2009.
PubChem Compound ID 38284487 May 29, 2009.
PubChem Compound ID 46438580 Jul. 23, 2010.
Siebeck et al., "Inhibition of Plasma Kallikrein With Aprotinin in Porcine Endotoxin Shock", The Journal of Trauma, 1993, vol. 34, No. 2, 193-198.
Stahl et al., "Handbook of Pharmaceutical Salts: Properties, Selection and Use", Wiley-VCH, Weinheim, Germany, 2002, 1 page.
STN Registry, "5-Pyrimidinecarboxamide, N-[1-(1H-benzimidazol-2-yl)ethyl]-1,6-dihydro-6-oxo-2-(phenoxymethyl)", CAS No. 1434334-41-4, Jun. 5, 2013.
Tang et al., "Expression, Crystallization, and Three-Dimensional Structure of the Catalytic Domain of Human Plasma Kallikrein" the Journal of Biological Chemistry, vol. 280, No. 49, Dec. 2005, pp. 41077-41089.
Tombran-Tink et al., "Opthamology Research", Visual Dysfunction in Diabetes the Science of Patient Impairment and Health Care, 2012, 4 pages.
Ulven et al.; "6-Acylamino-2-amino-4-methylquinolines as potent melanin-concentrating hormone 1 receptor antagonists: Structure-activity exploration of eastern and western parts"; Bioorganic & Medicinal Chemistry Letters; vol. 16 Issue 4; Feb. 2006; pp. 1070-1075.
Wermuth et al., Handbook of Pharmaceutical Salts: Properties, Selection and Use, 2002 vol. 24, No. 3, p. 20.
Wermuth, "The Practice of Medicinal Chemistry", 2003, 2nd Ed., pp. 561-585.
Ambinter Sari: "1 H-Pyrazole-4-carboxamides" In: Chemical Catalog, 11; Sep. 2011 (Sep. 11, 2011), Ambinter SARL, XP055601375.
Babu, "Drug Discovery at BioCryst Pharmaceuticals Inc.", Presentation, http://files.shareholder.com/downloads/BCRX/0x0x403076/97a18d6e-1621-4fc6--8f5fd0828bddab4f/, Sep. 16, 2010, 18 pages.
Bjorkqvist et al., "Plasma kallikrein: the bradykinin-producing enzyme", Thrombosis and Haemotasis, 2013, 110, 399-407.
Caddick et al., "Convenient Synthesis of Protected Primary Amines from Nitriles", Tetrahedron Letters, Apr. 29, 2000, 41(18), 3513-3516.
Calderone et al., "1,2,3-Triazol-Carboxanilides and 1,2,3-Triazol-(N-Benzyl)-Carboxamides as BK-Potassium Channel Activators. XII" European Journal of Medicinal Chemistry 43, 2008, pp. 2618-2626.
Cannon, Chapter Nineteen in Burger's Medicinal Chemistry and Drug Discovery, Fifth Edition, vol. I: Principles and Practice, Wiley-Interscience 1995, pp. 783-802.
CAS abstract accession No. 1990:515202, corresponding to Ried et al. Liebigs Annalen der Chemie, 1990, 8, 2 pages.
CAS abstract accession No. 2013:1177162, corresponding to Ye et al. Chemical Science, 2013, 4(9), 4 pages.
CAS abstract accession No. 2013:1592386, corresponding to FR2989085 A1 (Commissariat Energie Atomique), 3 pages Oct. 11, 2013.
CAS abstract accession Nos. 2009:769551 and 2009:846114, corresponding to U.S. Pub. No. 2009-0163545A1, 5 pages Jun 25, 2009.
CAS extract for Compound 1180236-10-5; Sep. 4, 2009.
CAS extract for Compound 1180808-34-7; Sep. 6, 2009.
CAS Extract for Compound 1197490-19-9, dated Dec. 16, 2009, 1 page.
CAS Extract for Compound 120842-43-4, dated Apr. 18, 2011, 1 page.
CAS extract for Compound 1288265-35-9; May 1, 2011.
CAS extract for Compound 1288488-40-3; May 1, 2011.
CAS extract for Compound 1288531-53-2; May 1, 2011.
CAS extract for Compound 1293757-54-6; May 12, 2011.
CAS extract for Compound 1297493-36-7; May 19, 2011.
CAS Extract for Compound 1386962-55-5, dated Aug. 6, 2012, 1 page.
CAS Extract for Compound 1388550-15-9, dated Aug. 9, 2012, 1 page.
CAS Extract for Compound 1626023-22-0, dated Sep. 25, 2014, 1 page.
CAS Structures cited in WO201683818 Written Opinion dated Jun. 2, 2016, 290 pages.
Chemical Abstract Service, Chemcats, RN 1424383-07-2, Mar. 15, 2013.
Chemical Abstracts Registry No. 1147797-44-1, indexed in the Registry file on STN CAS Online May 20, 2009.
Chemical Abstracts Registry No. 1217027-87-6, indexed in the Registry file on STN CAS Online Apr. 5, 2010.
Chemical Abstracts Registry No. 1241137-33-6, indexed in the Registry file on STN CAS Online Sep. 15, 2010.
Chemical Abstracts Registry No. 1295467-87-6, indexed in the Registry file on STN CAS Online May 16, 2011.

(56) References Cited

OTHER PUBLICATIONS

Chemical Abstracts Registry No. 1296846-83-7, indexed in the Registry file on STN CAS Online May 18, 2011.
Chemical Abstracts Registry No. 1297526-11-4, indexed in the Registry file on STN CAS Online May 19, 2011.
Chemical Abstracts Registry No. 1389653-06-8, indexed in the Registry file on STN CAS Online Aug. 12, 2012.
Chemical Abstracts Registry No. 1575116-26-5, indexed in the Registry file on STN CAS Online Mar. 28, 2014.
Chemical Abstracts Registry No. 942731-43-3, indexed in the Registry file on STN CAS Online Jul. 19, 2007.
Chemical Abstracts Registry No. 955899-78-2, indexed in the Registry file on STN CAS Online on Nov. 25, 2007.
Colman, "Plasma and tissue kallikrein in arthritis and inflammatory bowel disease", Immunopharmacology, 1999, 43, 103-108.
Davis III et al., "Biological activities of C1 inhibitor", Molecular Immunology, 2008, 45, 4057-4063.
Enamine website on Jul. 25, 2013 from the Internet Archive Way Back Machine (https://web.archive.org/web.archive.org/web/20130725053127/http://www.enamine.net/index.php?option=com_content&task=view&id=22.
Feener at al., "Role of plasma kallikrein in diabetes and metabolism", Thrombosis and Haemostasis, Sep. 2013, 110(3), 434-441.
Ikeda et al., "Host Stromal Bradykinin B.sub2 Receptor Signaling Facilitates Tumor-Associated Angiogenesis and Tumor Growth", Cancer Research, Aug. 2004, 64, 5178-5185.
International Patent Application No. PCT/GB2015/053613: International Search Report dated Jun. 2, 2016, 5 pages.
International Patent Application No. PCT/GB2015/053613: Written Opinion dated Jun. 2, 2016, 9 pages.
International Search Report for PCT/GB2014/051592 completed Jul. 23, 2014.
Jaffa et al., "Plasma Prekallikrein a Risk Marker for Hypertension and Nephropathy in Type 1 Diabetes", Diabetes, May 2003, vol. 52, 1215-1221.
Kenniston, J Bio Chem, "Inhibition of Plasma Kallikrein by a Highly Specific Active Site Blocking Antibody", vol. 289 (34), 2014, 23596-23608.
Leinweber et al, "Possible Physiological Roles of Carboxylic Ester Hydrolases", Drug Metabolism Reviews, 1987, 18(4), 379-439.
Lussis et al.; "A single synthetic small molecule that generates force against a load"; Nature Nanotechnology; vol. 6; 2011; p. S1-S25 (Supplemental Information).
Luthin et al., "The Discovery of Novel Small Molecule Non-peptide Gonadotropin Releasing Hormone (GnRH) Receptor Antagonists" Bioorg Med Chem Lett, 12, 2002, pp. 3467-3470.
Pace, et al., "4-Hydroxy-5-pyrrolinone-3-carboxamide HIV-1 integrase inhibitors", Bioorganic & Medicinal Chemistry Letters., 18, Jun. 2008, pp. 3865-3869.
Patel, "Combination Therapy for Age-Related Macular Degeneration", Retina, Jun. 2009, 29(6), pp. S45-S48.
Prassas, "Unleashing the therapeutic potential of human kallikrein—related serine proteases", Nature Reviews Drug Discovery, vol. 14, 183-202, 2015.
STN Registry, "5-Pyrimidinecarboxamide, 1,6-dihydro-N-[1-(6-methyl-1H-1-benzimidazol-2-yl)ethyl]-2-oxo-2-(1H-1,2,4-triazol-1-ylmethyl)", CAS No. 1422635-37-7, Mar. 8, 2013.
Chilcote et al., "ASP-634: An Oral Drug Candidate for Diabetic Macular Edema", ARVO 2012 May 6-May 9, 2012, Fort Lauderdale, Florida, (Presentation 2240), 1 page.
Durairaj et al., "Prediction of Vitreal Half-Life Based on Drug Physiochemical Properties: Quantitative Structure-Pharmacokinetic Relationships (QSPKR)", Pharmaceutical Research, 2009, 26(5), 1236-1260.
Lieberman et al. Pharmaceutical Dosage Forms: Tablets, Second Edition, vol. 2, 1989, XP008099925; 15 pages (front page and list of contents included), 145-157.
Marra et al, "Solution Formulation Development of a VEGF Inhibitor for Intravitreal Injection", 2011, 12(1), 362-370.
Maurice, "Review: Practical Issues in Intravitreal Drug Delivery", Journal of Ocular Pharmacology and Therapeutics, 2001, 17(4), 393-401.
MedicineNet (2004) Web:<http://www.medterms.com>.
Stahl and Wermuth, "Handbook of Pharmaceutical Salts: Properties, Selection and Use", Wiley-VCH, Weinheim, Germany, 2002.
Zhang et al., "Discovery of Highly Potent Small Molecule Kallikrein Inhibitors", Medicinal Chemistry, 2006, vol. 2, No. 6, 545-553.

\* cited by examiner

POLYMORPHS OF N-[(6-CYANO-2-FLUORO)-3-METHOXYPHENYL)METHYL]-3-(METHOXYMETHYL)-1-({4-[(2-OXOPYRIDIN-1-YL)METHYL]PHENYL}METHYL) PYRAZOLE-4-CARBOXAMIDE AS KALLIKREIN INHIBITORS

CROSS-REFERENCE TO RELATED APPLICATIONS

This application is the National Stage of International Patent Application No. PCT/GB2017/051575, filed Jun. 1, 2017, which claims the benefit of Great Britain Patent Application No. 1609603.4, filed Jun. 1, 2016 and U.S. Provisional Patent Application No. 62/344,133, filed Jun. 1, 2016, the disclosures of each of which are incorporated herein by reference in their entireties.

The present invention relates to new polymorphs of a plasma kallikrein inhibitor, a pharmaceutical composition containing them and their use in therapy.

BACKGROUND TO THE INVENTION

Inhibitors of plasma kallikrein have a number of therapeutic applications, particularly in the treatment of retinal vascular permeability associated with diabetic retinopathy, diabetic macular edema and hereditary angioedema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Plasma kallikrein also plays a role in blood coagulation. The intrinsic coagulation cascade may be activated by factor XII (FXII). Once FXII is activated (to FXIIa), FXIIa triggers fibrin formation through the activation of factor XI (FXI) thus resulting in blood coagulation. Plasma kallikrein is a key component in the intrinsic coagulation cascade because it activates FXII to FXIIa, thus resulting in the activation of the intrinsic coagulation pathway. Furthermore, FXIIa also activates further plasma prekallikrein resulting in plasma kallikrein. This results in positive feedback amplification of the plasma kallikrein system and the intrinsic coagulation pathway (Tanaka et al. (*Thrombosis Research* 2004, 113, 333-339); Bird et al. (*Thrombosis and Haemostasis*, 2012, 107, 1141-50).

Contact of FXII in the blood with negatively charged surfaces (such as the surfaces of external pipes or the membrane of the oxygenator that the blood passes during cardiopulmonary bypass surgery) induces a conformational change in zymogen FXII resulting in a small amount of active FXII (FXIIa). The formation of FXIIa triggers the formation of plasma kallikrein resulting in blood coagulation, as described above. Activation of FXII to FXIIa can also occur in the body by contact with negatively charged surfaces on various sources (e.g. bacteria during sepsis, RNA from degrading cells), thus resulting in disseminated intravascular coagulation (Tanaka et al. (*Thrombosis Research* 2004, 113, 333-339)).

Therefore, inhibition of plasma kallikrein would inhibit the blood coagulation cascade described above, and so would be useful in the treatment of disseminated intravascular coagulation and blood coagulation during cardiopulmonary bypass surgery where blood coagulation is not desired. For example, Katsuura et al. (*Thrombosis Research*, 1996, 82, 361-368) showed that administration of a plasma kallikrein inhibitor, PKSI-527, for LPS-induced disseminated intravascular coagulation significantly suppressed the decrease in platelet count and fibrinogen level as well as the increase in FDP level which usually occur in disseminated intravascular coagulation. Bird et al. (*Thrombosis and Haemostasis*, 2012, 107, 1141-50) showed that clotting time increased, and thrombosis was significantly reduced in plasma kallikrein-deficient mice. Revenko et al. (*Blood*, 2011, 118, 5302-5311) showed that the reduction of plasma prekallikrein levels in mice using antisense oligonucleotide treatment resulted in antithrombotic effects. Tanaka et al. (Thrombosis Research 2004, 113, 333-339) showed that contacting blood with DX-88 (a plasma kallikrein inhibitor) resulted in an increase in activated clotting time (ACT). Lehmann et al. (*Expert Opin. Biol. Ther.* 2008, 1187-99) showed that Ecallantide (a plasma kallikrein inhibitor) was found to delay contact activated induced coagulation. Lehmann et al. conclude that Ecallantide "had in vitro anticoagulant effects as it inhibited the intrinsic pathway of coagulation by inhibiting plasma kallikrein".

Plasma kallikrein also plays a role in the inhibition of platelet activation, and therefore the cessation of bleeding. Platelet activation is one of the earliest steps in hemostasis, which leads to platelet plug formation and the rapid cessation of bleeding following damage to blood vessels. At the site of vascular injury, the interaction between the exposed collagen and platelets is critical for the retention and activation of platelets, and the subsequent cessation of bleeding.

Once activated, plasma kallikrein binds to collagen and thereby interferes with collagen-mediated activation of platelets mediated by GPVI receptors (Liu et al. (*Nat Med.*, 2011, 17, 206-210)). As discussed above, plasma kallikrein inhibitors reduce plasma prekallikrein activation by inhibiting plasma kallikrein-mediated activation of factor XII and thereby reducing the positive feedback amplification of the kallikrein system by the contact activation system.

Therefore, inhibition of plasma kallikrein reduces the binding of plasma kallikrein to collagen, thus reducing the interference of plasma kallikrein in the cessation of bleeding. Therefore plasma kallikrein inhibitors would be useful in the treatment of treating cerebral haemorrhage and bleeding from post operative surgery. For example, Liu et al. (*Nat Med.*, 2011, 17, 206-210) demonstrated that systemic administration of a small molecule PK inhibitor, ASP-440, reduced hematoma expansion in rats. Cerebral hematoma may occur following intracerebral haemorrhage and is caused by bleeding from blood vessels into the surrounding brain tissue as a result of vascular injury. Bleeding in the cerebral haemorrhage model reported by Liu et al. was induced by surgical intervention involving an incision in the brain parenchyma that damaged blood vessels. These data demonstrate that plasma kallikrein inhibition reduced bleeding and hematoma volume from post operative surgery. Björkqvist et al. (*Thrombosis and Haemostasis*, 2013, 110, 399-407) demonstrated that aprotinin (a protein that inhibits serine proteases including plasma kallikrein) may be used to decrease postoperative bleeding.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . " *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (*Brazilian J. Med. Biol. Res* 27, p 1929-34 (1994)), Kettner et al. (US 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem. Letts.* 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. Many of the molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote and Sukanto Sinha ("ASP-634: An Oral Drug Candidate for Diabetic MacularEdema", ARVO 2012 May 6$^{th}$-May 9$^{th}$, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites. In another report, indole amides are claimed as compounds that might overcome problems associated with drugs possessing poor or inadequate ADME-tox and physicochemical properties although no inhibition against plasma kallikrein is presented or claimed (Griffioen et al, "Indole amide derivatives and related compounds for use in the treatment of neurodegenerative diseases", WO2010/142801).

BioCryst Pharmaceuticals Inc. have reported the discovery of the orally available plasma kallikrein inhibitor BCX4161 ("BCX4161, An Oral Kallikrein Inhibitor: Safety and Pharmacokinetic Results Of a Phase 1 Study In Healthy Volunteers", Journal of Allergy and Clinical Immunology, Volume 133, Issue 2, Supplement, February 2014, page AB39 and "A Simple, Sensitive and Selective Fluorogenic Assay to Monitor Plasma Kallikrein Inhibitory Activity of BCX4161 in Activated Plasma", Journal of Allergy and Clinical Immunology, Volume 133, Issue 2, Supplement February 2014, page AB40). However, human doses are relatively large, currently being tested in proof of concept studies at doses of 400 mg three times daily.

There are only few reports of plasma kallikrein inhibitors that do not feature guanidine or amidine functionalities. One example is Brandi et al. ("N-((6-amino-pyridin-3-yl) methyl)-heteroaryl-carboxamides as inhibitors of plasma kallikrein" WO2012/017020), which describes compounds that feature an amino-pyridine functionality. Oral efficacy in a rat model is demonstrated at relatively high doses of 30 mg/kg and 100 mg/kg but the pharmacokinetic profile is not reported. Thus it is not yet known whether such compounds will provide sufficient oral availability or efficacy for progression to the clinic. Other examples are Brandi et al. ("Aminopyridine derivatives as plasma kallikrein inhibitors" WO2013/111107) and Flohr et al. ("5-membered heteroarylcarboxamide derivatives as plasma kallikrein inhibitors" WO2013/111108). However, neither of these documents report any in vivo data and therefore it is not yet known whether such compounds will provide sufficient oral availability or efficacy for progression to the clinic. Another example is Allan et al. "Benzylamine derivatives" WO2014/108679.

In the manufacture of pharmaceutical formulations, it is important that the active compound be in a form in which it can be conveniently handled and processed in order to obtain a commercially viable manufacturing process. Accordingly, the chemical stability and the physical stability of the active compound are important factors. The active compound, and formulations containing it, must be capable of being effectively stored over appreciable periods of time, without exhibiting any significant change in the physicochemical characteristics (e.g. chemical composition, density, hygroscopicity and solubility) of the active compound.

It is known that manufacturing a particular solid-state form of a pharmaceutical ingredient can affect many aspects of its solid state properties and offer advantages in aspects of solubility, dissolution rate, chemical stability, mechanical properties, technical feasibility, processability, pharmacokinetics and bioavailability. Some of these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are also described in "Practical Process Research and Development", Neal G. Anderson (Academic Press, San Diego) and "Polymorphism: In the Pharmaceutical Industry", Rolf Hilfiker (Ed) (Wiley VCH). Polymorphism in pharmaceutical crystals is described in Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

The applicant has developed a novel series of compounds that are inhibitors of plasma kallikrein, which are disclosed in WO2016/083820 (PCT/GB2015/053615). These compounds demonstrate good selectivity for plasma kallikrein and are potentially useful in the treatment of diabetic retinopathy, macular edema and hereditary angioedema. One such compound is N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide. Initial attempts to prepare N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide yielded a yellow foam. However, the applicant has now developed novel, stable crystalline forms of this compound, which are herein referred to as 'Form 1', 'Form 2', 'Form 3', and 'Form 4'. The novel solid forms have advantageous physicochemical properties that render them suitable for development.

DESCRIPTION OF THE INVENTION

Thus, in accordance with an aspect of the present invention, there is provided crystalline polymorphs of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide. In the present application these polymorphs may be referred to as 'Form 1', 'Form 2', 'Form 3' and 'Form 4'.

The crystalline polymorphs of the present invention have advantageous physico-chemical properties that render them suitable for development For example, the absence of weight loss before melt of the sample of Form 1 (see STA data, FIG. 2) indicates that Form 1 is not hydrated or solvated. Stable hydrates may be unsuitable for pharmaceutical development because they are often less soluble than anhydrates or they may induce an undesirable transformation of the administered anhydrous form of the drug once the drug meets the aqueous environment of the human body. Another advantage of the crystalline polymorphs is that they are more easily processable. That is, their preparation by crystallisation (see Examples) is a common and easily scalable procedure to remove undesirable impurities.

The name N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide denotes the structure depicted in Formula A.

Formula A

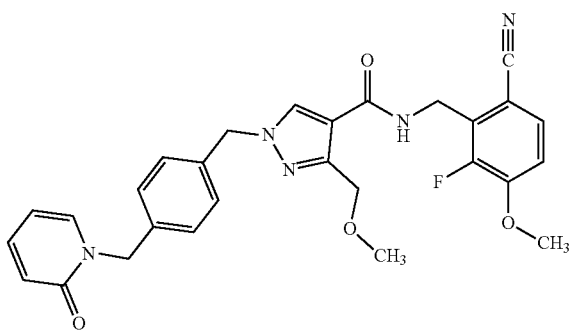

The present invention encompasses solvates (e.g. hydrates) of the crystalline forms of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide.

In an aspect of the invention, the crystalline forms of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide are not solvates or hydrates.

Four crystalline polymorphs of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide have been isolated and characterised to date, which are herein referred to as 'Form 1', 'Form 2', 'Form 3', and 'Form 4'. Preferably, the crystalline form is Form 1.

In the present specification, X-ray powder diffraction peaks (expressed in degrees 2θ) are measured using Cu Kα radiation.

The present invention provides a crystalline form (Form 1) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, which exhibits at least the following characteristic X-ray powder diffraction peaks (Cu Kα radiation, expressed in degrees 2θ) at approximately:

(1) 9.0, 14.3, 18.1, 19.6 and 24.0; or
(2) 9.0, 14.3, 18.1, 19.6, 21.3, 24.0 and 27.1; or
(3) 9.0, 14.3, 18.1, 19.6, 21.3, 23.5, 24.0, 27.1 and 28.5.

The term "approximately" means in this context that there is an uncertainty in the measurements of the degrees 2θ of ±0.3 (expressed in degrees 2θ), preferably ±0.2 (expressed in degrees 2θ).

The present invention also provides a crystalline form (Form 1) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, having an X ray powder diffraction pattern comprising characteristic peaks (expressed in degrees 2θ) at approximately 9.0, 14.3, 15.4, 18.1, 19.0, 19.6, 21.3, 23.5, 24.0, 27.1 and 28.5.

FIG. 1 shows an X-ray powder diffraction pattern of Form 1 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide. The present invention also provides a crystalline form (Form 1) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide having an X-ray powder diffraction pattern substantially the same as that shown in FIG. 1.

The X-ray powder diffraction pattern of a polymorphic form may be described herein as "substantially" the same as that depicted in a Figure. It will be appreciated that the peaks in X-ray powder diffraction patterns may be slightly shifted in their positions and relative intensities due to various factors known to the skilled person. For example, shifts in peak positions or the relative intensities of the peaks of a pattern can occur because of the equipment used, method of sample preparation, preferred packing and orientations, the radiation source, and method and length of data collection. However, the skilled person will be able to compare the X-ray powder diffraction patterns shown in the figures herein with those of an unknown polymorph to confirm the identity of the polymorph.

The present invention also provides a crystalline form (Form 2) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, which exhibits at least the following characteristic X-ray powder diffraction peaks (Cu Kα radiation, expressed in degrees 2θ) at approximately:

(1) 8.3, 10.5, 16.6, 19.6 and 23.8; or
(2) 8.3, 10.5, 11.7, 16.6, 17.5, 19.6 and 23.8; or
(3) 8.3, 10.5, 11.7, 16.6, 17.5, 19.6, 20.9, 23.8 and 28.4.

The present invention also provides a crystalline form (Form 2) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, having an X ray powder diffraction pattern comprising characteristic peaks (expressed in degrees 2θ) at approximately 8.3, 10.5, 11.7, 15.6, 16.6, 17.5, 19.6, 20.9, 21.8, 23.8, 27.9, 28.4 and 28.9.

Figure 5:
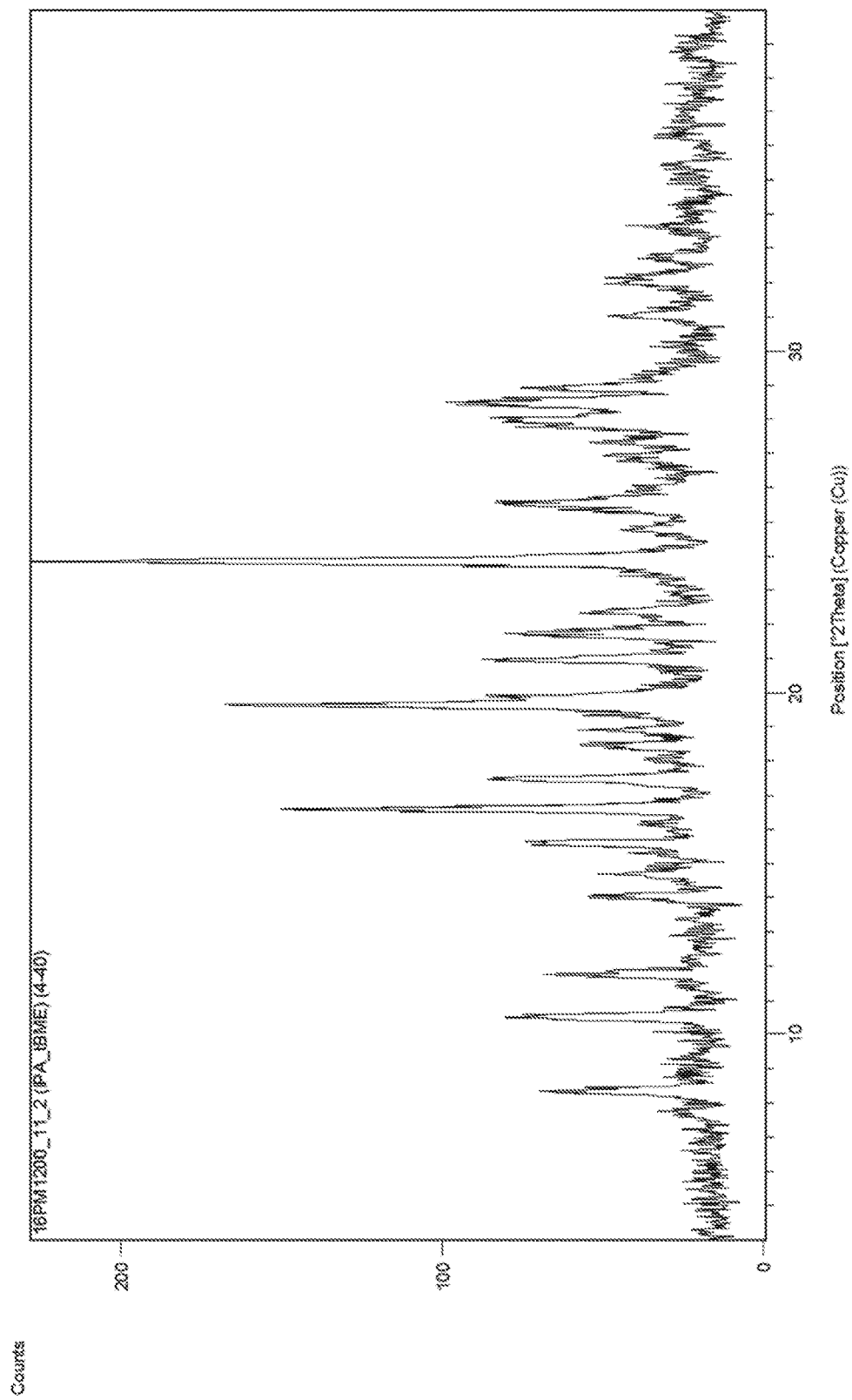

FIG. 5 shows an X-ray powder diffraction pattern of Form 2 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide. The present invention also provides a crystalline form (Form 2) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide having an X-ray powder diffraction pattern substantially the same as that shown in FIG. 5.

The present invention also provides a crystalline form (Form 3) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, which exhibits at least the following characteristic X-ray powder diffraction peaks (Cu Kα radiation, expressed in degrees 2θ) at approximately:

(1) 7.3, 10.2, 12.4, 12.9 and 18.1; or
(2) 7.3, 10.2, 12.4, 12.9, 18.1, 22.1 and 24.0; or
(3) 7.3, 10.2, 12.4, 12.9, 13.7, 18.1, 18.8, 22.1 and 24.0.

The present invention also provides a crystalline form (Form 3) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, having an X ray powder diffraction pattern comprising characteristic peaks (expressed in degrees 2θ) at approximately 7.3, 10.2, 12.4, 12.9, 13.7, 17.6, 18.1, 18.8, 22.1 and 24.0

Figure 6:
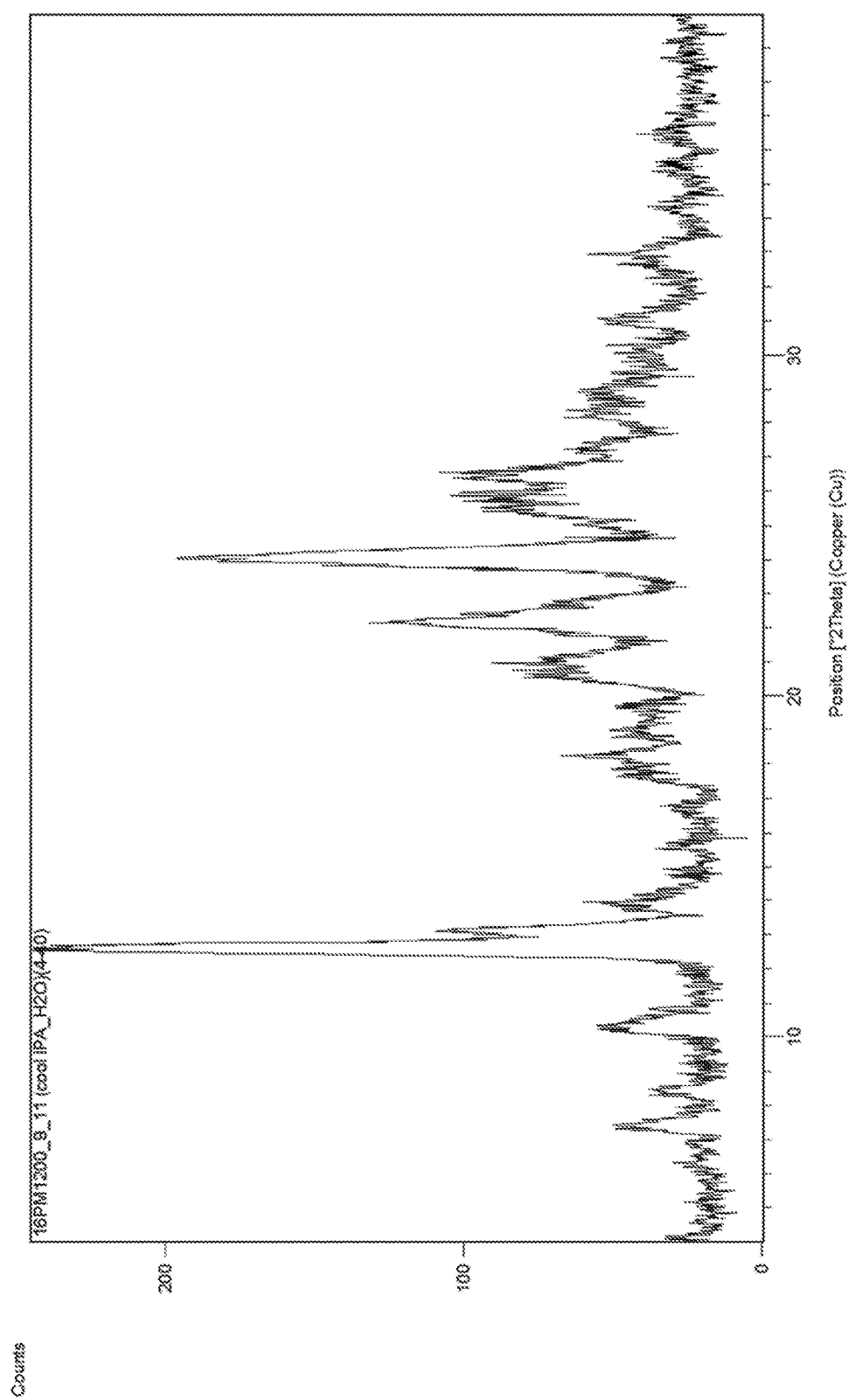

FIG. 6 shows an X-ray powder diffraction pattern of Form 3 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide. The present invention also provides a crystalline form (Form 3) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide having an X-ray powder diffraction pattern substantially the same as that shown in FIG. 6.

The present invention also provides a crystalline form (Form 4) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, which exhibits at least the following characteristic X-ray powder diffraction peaks (Cu Kα radiation, expressed in degrees 2θ) at approximately:

(1) 9.0, 14.3, 15.0, 18.1 and 19.5; or
(2) 9.0, 14.3, 15.0, 18.1, 18.9, 19.5, and 27.0; or
(3) 9.0, 14.3, 15.0, 16.0, 18.1, 18.9, 19.5, 24.0 and 27.0.

The present invention also provides a crystalline form (Form 4) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, having an X ray powder diffraction pattern comprising characteristic peaks (expressed in degrees 2θ) at approximately 9.0, 14.3, 15.0, 16.0, 18.1, 18.9, 19.5, 24.0, 25.3 and 27.0.

Figure 7:
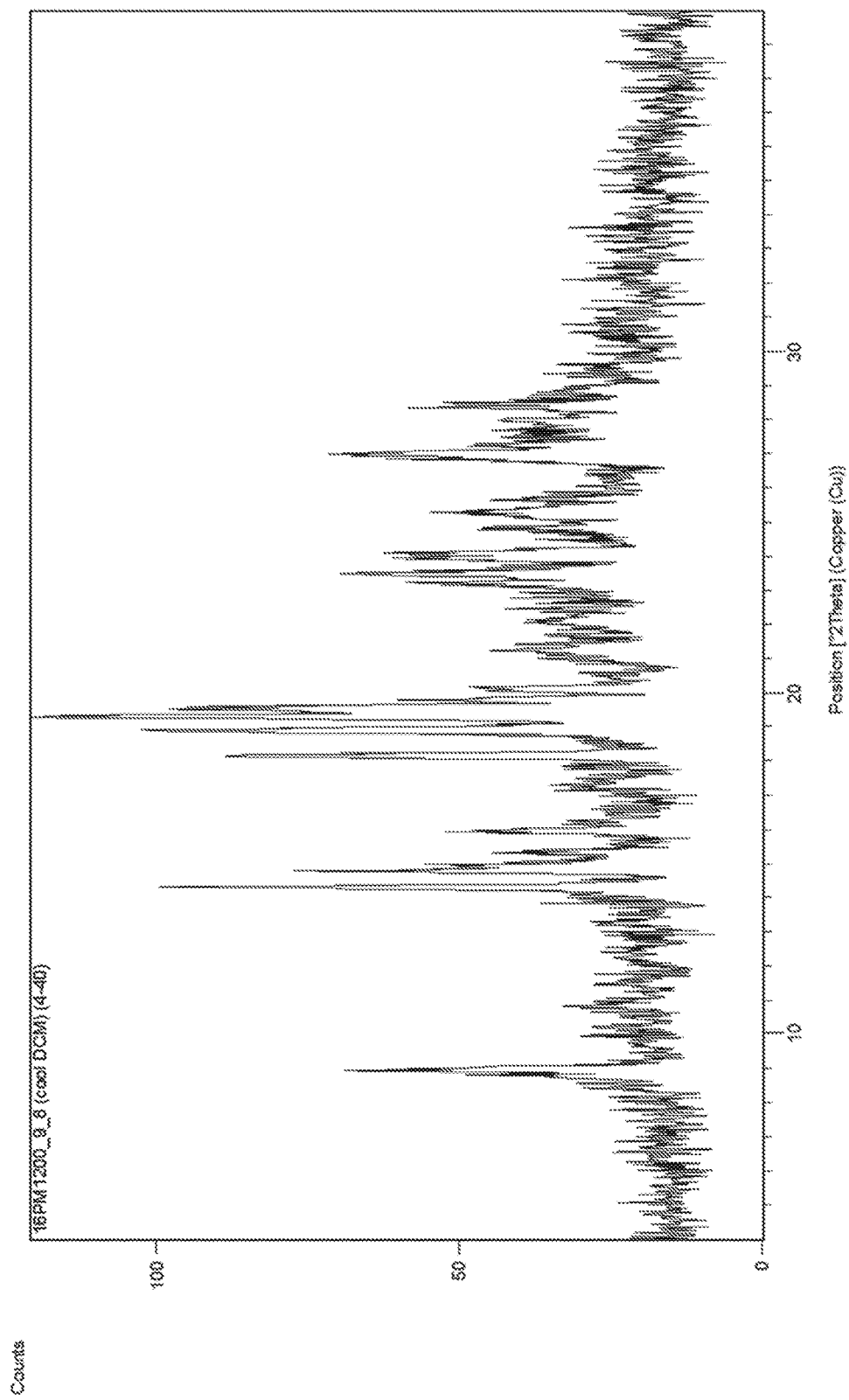

FIG. 7 shows an X-ray powder diffraction pattern of Form 4 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide. The present invention also provides a crystalline form (Form 4) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide having an X-ray powder diffraction pattern substantially the same as that shown in FIG. 7.

The skilled person is familiar with techniques for measuring XRPD patterns. In particular, the X-ray powder diffraction pattern of the sample of compound may be recorded using a Philips X-Pert MPD diffractometer with the following experimental conditions:

Tube anode: Cu;
Generator tension: 40 kV;
Tube current: 40 mA;
Wavelength alpha1: 1.5406 Å;
Wavelength alpha2: 1.5444 Å;
Sample: 2 mg of sample under analysis gently compressed on the XRPD zero back ground single obliquely cut silica sample holder.

The present invention provides a crystalline form (Form 1) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, which exhibits an endothermic peak in its DSC thermograph at 149±3° C., preferably 149±2° C., more preferably 149±1° C.

The present invention provides a crystalline form (Form 1) of N-[(6-cyano-2-fluoro-3-methoxyphenyl)methyl]-3-

Figure 3:
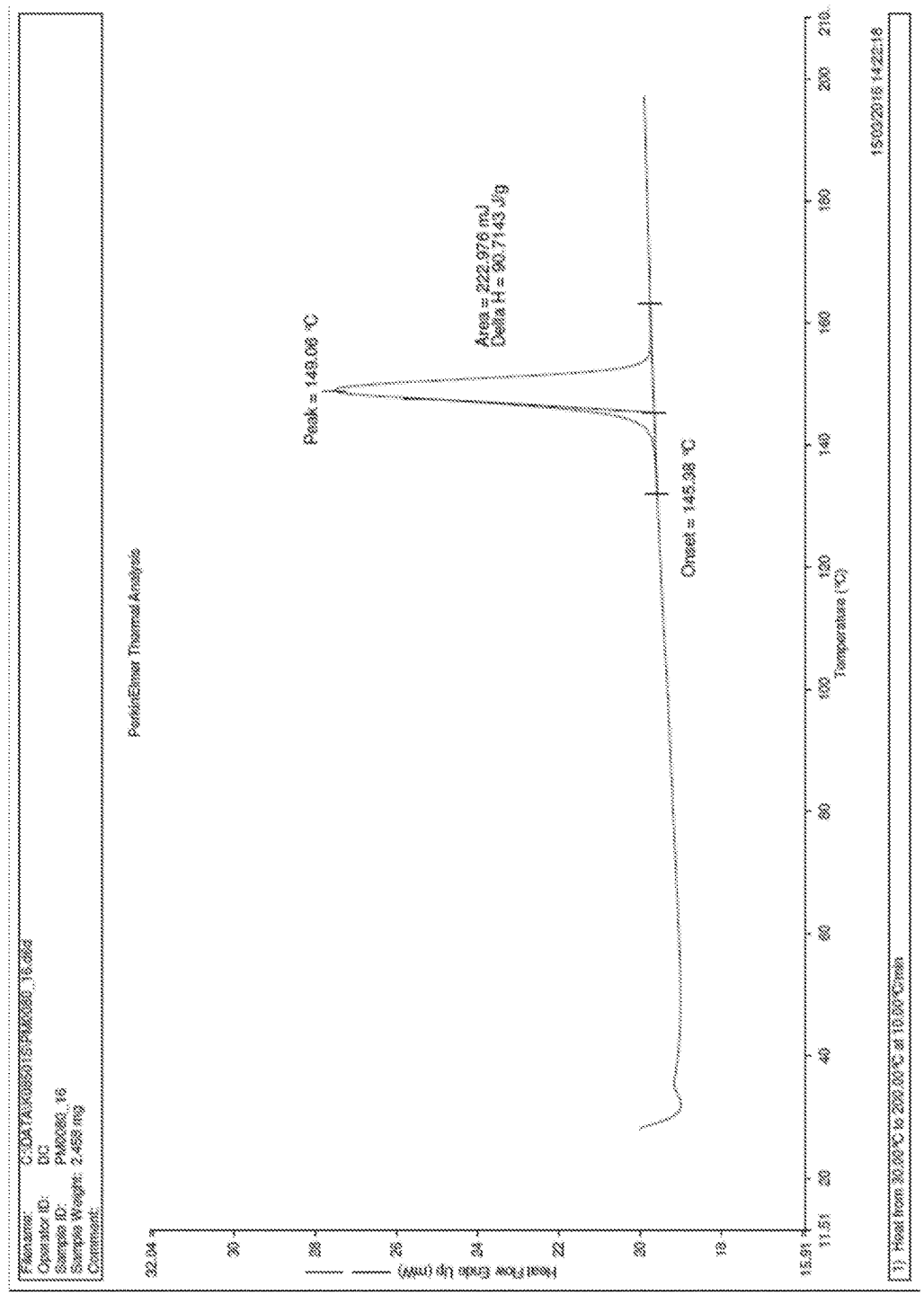

(methoxymethyl)-1-({4-[(2-oxopyridin-1-yl)methyl]phenyl}methyl)pyrazole-4-carboxamide, having a DSC thermograph substantially the same as that shown in FIG. 3.

The skilled person is familiar with techniques for measuring DSC thermographs. In particular, the DSC thermograph of the sample of compound may be recorded by (a) weighing 5 mg of the sample into an aluminium DSC pan and sealing non-hermetically with an aluminium lid;

(b) loading the sample into a Perkin-Elmer Jade DSC and holding the sample at 30° C. until a stable heat-flow response is obtained while using a 20 cm$^3$/min helium purge;

(c) heating the sample to a temperature of 200° C. at a scan rate of 10° C./min and monitoring the resulting heat flow response while using a 20 cm$^3$/min helium purge.

The present invention also provides a crystalline form (Form 1) of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide having an X-ray powder diffraction pattern as described above, and a DSC thermograph as described above.

The crystalline form of the present invention can exist in both unsolvated and solvated forms. The term 'solvate' is used herein to describe a molecular complex comprising the compound of the invention and an amount of one or more pharmaceutically acceptable solvents, for example, methanol. The term 'hydrate' is employed when the solvent is water.

A reference to a particular compound also includes all isotopic variants.

The present invention also encompasses a process for the preparation of Form 1 of the present invention, said process comprising the crystallisation of said crystalline form from a solution of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide in a solvent or a mixture of solvents. Preferably, the solvent is isopropanol. After adding the N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide to a solvent or a mixture of solvents (e.g. isopropanol), the combined mixture (compound plus solvent(s)) may be heated to a temperature of approximately 60-85° C. Alternatively, the combined mixture may be heated to a temperature of approximately 70-85° C. Alternatively, the combined mixture may be heated to a temperature of approximately 80-85° C. Alternatively, the combined mixture may be heated to a temperature of approximately 80, 81, 82, 83, 84 or 85° C. Alternatively, the combined mixture may be heated to a temperature of approximately 82° C. Alternatively, the combined mixture may be heated to reflux. Following heating, the combined mixture may be cooled. Alternatively, the combined mixture may be cooled to a temperature of approximately 0-40° C. Alternatively, the combined mixture may be cooled to a temperature of approximately 10-30° C. Alternatively, the combined mixture may be cooled to about 20° C.

The present invention also encompasses a process for the preparation of Form 2 of the present invention, said process comprising the crystallisation of said crystalline form from a solution of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide in a solvent or a mixture of solvents. Preferably, the solvent is isopropanol and methyl tert-butyl ether. After adding the N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide to a solvent or a mixture of solvents (e.g. isopropanol), the combined mixture (compound plus solvent(s)) may be added to an anti-solvent (e.g. methyl tert-butyl ether). Optionally, the combined mixture (compound plus solvent(s)) may be heated, and optionally filtered, prior to addition to the anti-solvent.

The present invention also encompasses a process for the preparation of Form 3 of the present invention, said process comprising the crystallisation of said crystalline form from a solution of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide in a solvent or a mixture of solvents. Preferably, the solvent is isopropanol and water. More preferably, the solvent is 90:10 isopropanol/water. After adding the N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide to a solvent or a mixture of solvents (e.g. isopropanol and water), the combined mixture (compound plus solvent(s)) may be heated before being allowed to cool. Alternatively, the combined mixture may be heated before being allowed to cool to a temperature of about 0 to –80° C. Alternatively, the combined mixture may be heated before being allowed to cool to a temperature of about –60 to –80° C. Alternatively, the combined mixture may be heated before being allowed to cool to a temperature of about –78° C. Alternatively, the combined mixture may be heated before being plunged into a dry ice/acetone bath. The cooled mixture may then be transferred to a freezer.

The present invention also encompasses a process for the preparation of Form 4 of the present invention, said process comprising the crystallisation of said crystalline form from a solution of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide in a solvent or a mixture of solvents. Preferably, the solvent is dichloromethane. After adding the N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide to a solvent or a mixture of solvents (e.g. dichloromethane), the combined mixture (compound plus solvent(s)) may be heated before being allowed to cool. Alternatively, the combined mixture may be heated before being allowed to cool to a temperature of about 0 to –80° C. Alternatively, the combined mixture may be heated before being allowed to cool to a temperature of about –60 to –80° C. Alternatively, the combined mixture may be heated before being allowed to cool to a temperature of about –78° C. Alternatively, the combined mixture may be heated before being plunged into a dry ice/acetone bath. The cooled mixture may then be transferred to a freezer.

The present invention also encompasses a process for the preparation of Form 4 of the present invention, said process comprising the crystallisation of said crystalline form from a solution of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide in a solvent or a mixture of solvents. Preferably, the solvent is anisole and methyl tert-butyl ether. After adding the N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide to a solvent or a mixture of solvents (e.g. anisole), the combined mixture (compound plus solvent(s)) may be added to an anti-solvent (e.g. methyl tert-butyl ether). Optionally, the combined mixture (compound plus solvent(s)) may be heated, and optionally filtered, prior to addition to the anti-solvent.

The processes of the present invention may also comprise the addition of crystalline seeds of the crystal form of the invention.

In an aspect, the present invention provides the crystalline form of the invention when manufactured by a process according to the invention.

As previously mentioned, the crystalline form of the present invention has a number of therapeutic applications, particularly in the treatment of diseases or conditions mediated by plasma kallikrein.

Accordingly, the present invention provides a crystalline form of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, as hereinbefore defined, for use in therapy. In a preferred embodiment, the crystalline form is Form 1.

The present invention also provides for the use of a crystalline form of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, as hereinbefore defined, in the manufacture of a medicament for the treatment of a disease or condition mediated by plasma kallikrein. In a preferred embodiment, the crystalline form is Form 1.

The present invention also provides a crystalline form of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, as hereinbefore defined, for use in a method of treatment of a disease or condition mediated by plasma kallikrein. In a preferred embodiment, the crystalline form is Form 1.

The present invention also provides a method of treatment of a disease or condition mediated by plasma kallikrein, said method comprising administering to a mammal in need of such treatment a therapeutically effective amount of a crystalline form of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide, as hereinbefore defined. In a preferred embodiment, the crystalline form is Form 1.

In an aspect, the disease or condition mediated by plasma kallikrein is selected from impaired visual acuity, diabetic retinopathy, retinal vascular permeability associated with diabetic retinopathy, diabetic macular edema, hereditary angioedema, diabetes, pancreatitus, cerebral haemorrhage, nepropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery and bleeding from post-operative surgery. In a preferred embodiment, the disease or condition mediated by plasma kallikrein is diabetic macular edema. In another preferred embodiment, the disease or condition mediated by plasma kallikrein is hereditary angioedema.

In another aspect, the disease or condition in which plasma kallikrein activity is implicated is retinal vein occlusion.

Alternatively, the disease or condition mediated by plasma kallikrein may be selected from retinal vascular permeability associated with diabetic retinopathy, diabetic macular edema and hereditary angioedema. Alternatively, the disease or condition mediated by plasma kallikrein may be retinal vascular permeability associated with diabetic retinopathy or diabetic macular edema. Alternatively, the disease or condition mediated by plasma kallikrein may be hereditary angioedema. The crystalline form of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide may be administered in a form suitable for injection into the ocular region of a patient, in particular, in a form suitable for intra-vitreal injection.

In the context of the present invention, references herein to "treatment" include references to curative, palliative and prophylactic treatment, unless there are specific indications to the contrary. The terms "therapy", "therapeutic" and "therapeutically" should be construed in the same way.

The crystalline form of the present invention may be administered alone or in combination with one or more other drugs. Generally, it will be administered as a formulation in association with one or more pharmaceutically acceptable excipients. The term "excipient" is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema".Ophthalmology. 27 Apr. 2010).

Pharmaceutical compositions suitable for the delivery of the crystalline form of the present invention and methods for their preparation will be readily apparent to those skilled in the art. Such compositions and methods for their preparation may be found, for example, in Remington's Pharmaceutical Sciences, 19th Edition (Mack Publishing Company, 1995).

For administration to human patients, the total daily dose of the crystalline form of the invention is typically in the range 0.1 mg and 10,000 mg, or between 1 mg and 5000 mg, or between 10 mg and 1000 mg depending, of course, on the mode of administration. If administered by intra-vitreal injection a lower dose of between 0.0001 mg (0.1 µg) and 0.2 mg (200 µg) per eye is envisaged, or between 0.0005 mg (0.5 µg) and 0.05 mg (50 µg) per eye.

The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Accordingly, the present invention provides a pharmaceutical composition comprising a crystalline solid form of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, as hereinbefore defined, and a pharmaceutically acceptable carrier, diluent or excipient. In a preferred embodiment, the crystalline solid form is Form 1.

The pharmaceutical compositions may be administered topically (e.g. to the eye, to the skin or to the lung and/or airways) in the form, e.g., of eye-drops, creams, solutions, suspensions, heptafluoroalkane (HFA) aerosols and dry powder formulations; or systemically, e.g. by oral administration in the form of tablets, capsules, syrups, powders or granules; or by parenteral administration in the form of solutions or suspensions; or by subcutaneous administration;

or by rectal administration in the form of suppositories; or transdermally. In a further embodiment, the pharmaceutical composition is in the form of a suspension, tablet, capsule, powder, granule or suppository.

In an embodiment of the invention, the active ingredient is administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the crystalline form in an immediate release manner or in a rate-sustaining manner, wherein the release profile can be delayed, pulsed, controlled, sustained, or delayed and sustained or modified in such a manner which optimises the therapeutic efficacy of the said crystalline form. Means to deliver compounds in a rate-sustaining manner are known in the art and include slow release polymers that can be formulated with the said compounds to control their release.

Liquid (including multiple phases and dispersed systems) formulations include emulsions, suspensions, solutions, syrups and elixirs. Such formulations may be presented as fillers in soft or hard capsules. Liquid formulations may also be prepared by the reconstitution of a solid, for example, from a sachet.

The crystalline form of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

The invention will now be illustrated by the following non-limiting examples. In the examples the following figures are presented:

FIG. 1: X-ray powder diffraction pattern of Form 1 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide.

Figure 2:
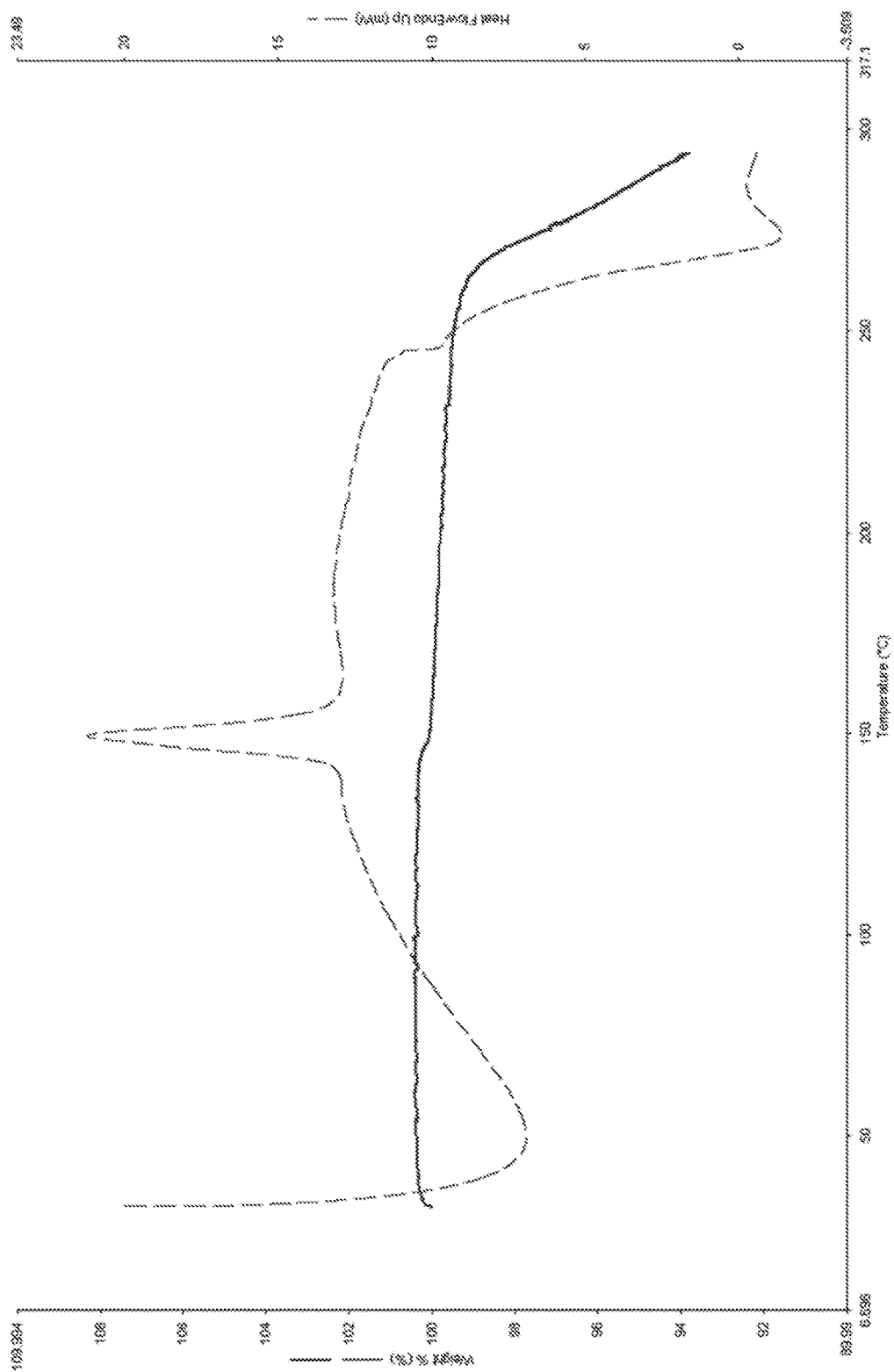

FIG. 2: STA of Form 1 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide.

FIG. 3: DSC thermograph of Form 1 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide.

Figure 4A:
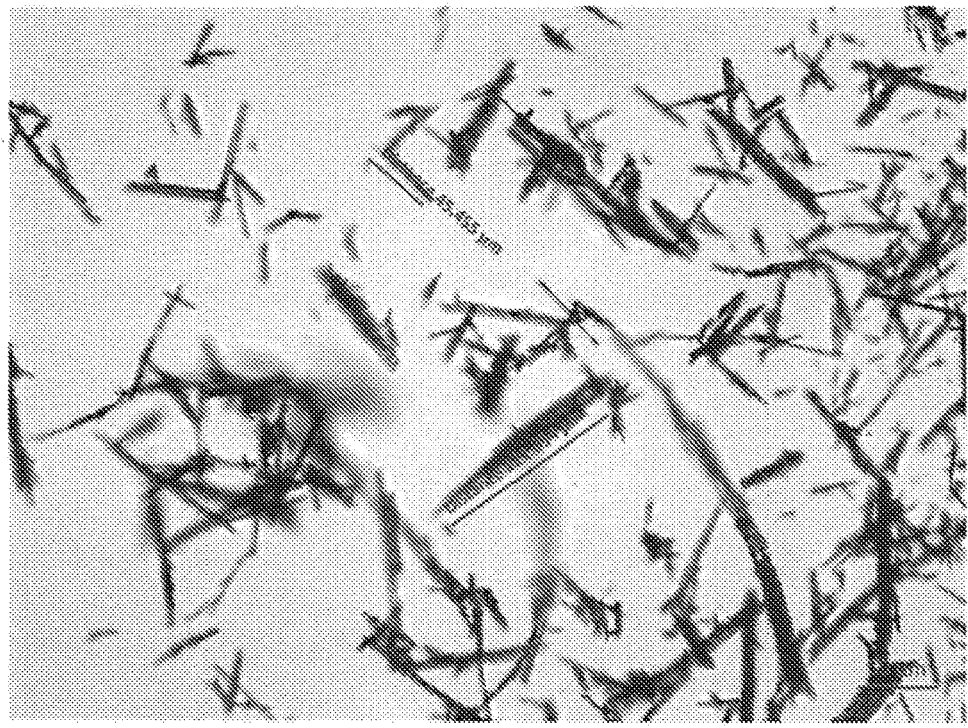
Figure 4B:
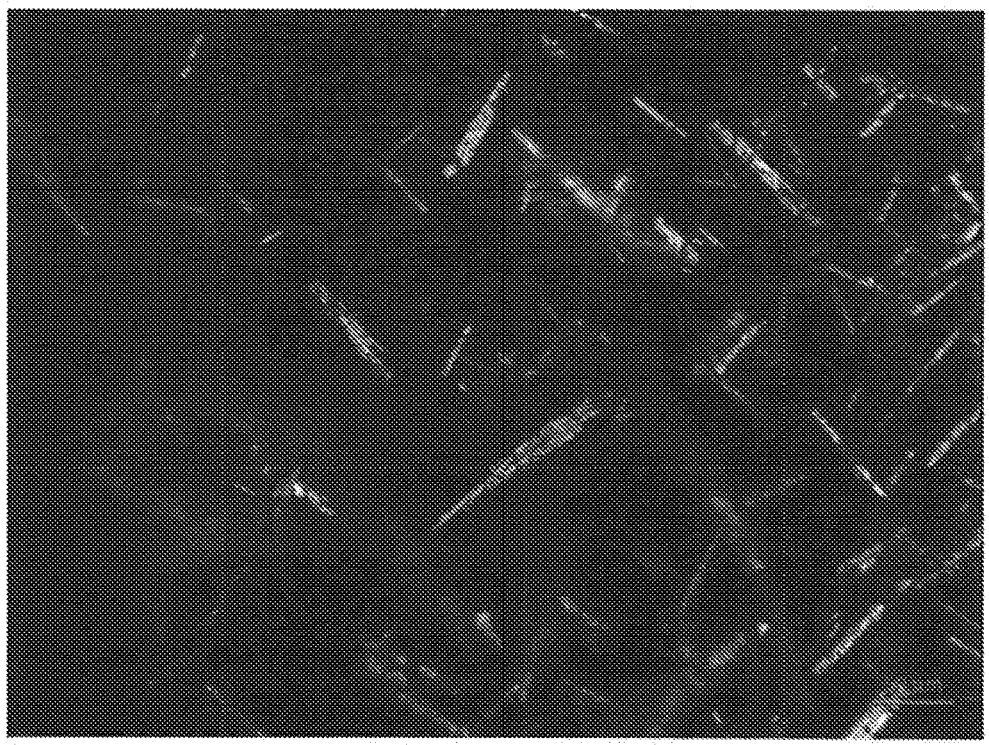

FIG. 4(a): Microscopy image (enlarged 100x) of Form 1.
FIG. 4(b): Polarized image of Form 1.
FIG. 5: X-ray powder diffraction pattern of Form 2 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide.

FIG. 6: X-ray powder diffraction pattern of Form 3 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide.

FIG. 7: X-ray powder diffraction pattern of Form 4 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide.

GENERAL EXPERIMENTAL DETAILS

In the following examples, the following abbreviations and definitions are used:

| | |
|---|---|
| aq | Aqueous solution |
| DCM | Dichloromethane |
| DMF | N,N-Dimethylformamide |
| DMSO | Dimethyl sulfoxide |
| DSC | Differential Scanning Calorimetry |
| EtOAc | Ethyl Acetate |
| HATU | 2-(3H-[1,2,3]triazolo[4,5-b]pyridin-3-yl)-1,1,3,3-tetramethylisouronium hexafluorophosphate(V) |
| hrs | Hours |
| HOBt | Hydroxybenzotriazole |
| IPA | Isopropanol |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum - NMR spectra were recorded at a frequency of 400 MHz unless otherwise indicated |
| Pet. Ether | Petroleum ether fraction boiling at 60-80° C. |
| Ph | Phenyl |
| STA | Simultaneous Thermal Analysis |
| SWFI | Sterile water for injection |
| rt | room temperature |
| THF | Tetrahydrofuran |
| TFA | Trifluoroacetic acid |
| XRPD | X-ray powder diffraction |

All reactions were carried out under an atmosphere of nitrogen unless specified otherwise.

$^1$H NMR spectra were recorded on a Bruker (400 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% HCO$_2$H/MeCN into 0.1% HCO$_2$H/H$_2$O over 13 min, flow rate 1.5 mL/min, or using Agilent, X-Select, acidic, 5-95% MeCN/water over 4 min. Data was collected using a Thermofinnigan Surveyor MSQ mass spectrometer with electrospray ionisation in conjunction with a Thermofinnigan Surveyor LC system.

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Chemical names were generated using automated software such as the Autonom software provided as part of the ISIS Draw package from MDL Information Systems or the Chemaxon software provided as a component of MarvinSketch or as a component of the IDBS E-WorkBook.

X-Ray Powder Diffraction patterns were collected on a Philips X-Pert MPD diffractometer and analysed using the following experimental conditions:

Tube anode: Cu
Generator tension: 40 kV
Tube current: 40 mA
Wavelength alpha1: 1.5406 Å
Wavelength alpha2: 1.5444 Å
Start angle [2θ]: 4
End angle [2θ]: 40
Continuous scan Approximately 2 mg of sample under analysis was gently compressed on the XRPD zero back ground single obliquely cut silica sample holder. The sample was then loaded into the diffractometer for analysis.

DSC data were collected using the following method: Approximately 5 mg of each sample was weighed into an aluminium DSC pan and sealed non-hermetically with an aluminium lid. The sample was then loaded into a Perkin-Elmer Jade DSC and held at 30° C. Once a stable heat-flow response was obtained, the sample was then heated to a temperature between 200 and 300° C. at a scan rate of 10° C./min and the resulting heat flow response was monitored. A 20 cm$^3$/min helium purge was used. Prior to analysis, the instrument was temperature and heat flow verified using an indium standard.

Simultaneous Thermal Analysis (STA) data were collected using the following method: Approximately 5 mg of sample was accurately weighed into a ceramic crucible and it was placed into the chamber of Perkin-Elmer STA 600 TGA/DTA analyzer at ambient temperature. The sample was then heated at a rate of 10° C./min, typically from 25° C. to 300° C., during which time the change in weight was monitored as well as DTA signal. The purge gas used was nitrogen at a flow rate of 20 cm$^3$/min.

Synthetic Examples

6-Bromo-2-fluoro-3-methoxy-benzoic acid

To a suspension of 2-fluoro-3-methoxybenzoic acid (10 g, 58.8 mmol) in acetic acid (50 mL) and water (50 mL) at rt was added bromine (6.06 mL, 118 mmol) dropwise. The reaction was then heated to 60° C. for 1 hr. The reaction was cooled to room temperature and the white precipitate was filtered. The solid was washed with water (200 mL) and iso-Hexane (50 mL) to give 6-bromo-2-fluoro-3-methoxy-benzoic acid as white solid, 12.098 g, 82% yield.
[MH]$^+$=249/251

(6-Bromo-2-fluoro-3-methoxy-phenyl)-methanol

To a stirred solution of 6-bromo-2-fluoro-3-methoxy-benzoic acid (4.13 g, 16.58 mmol) in THF (20 mL) was added 4-methylmorpholine (1.914 mL, 17.41 mmol) and then isobutyl chloroformate (2.15 mL, 16.58 mmol). After 1 hour the reaction mixture was filtered to remove any salts generated, the solid was washed with additional THF (10 mL). The filtrate and washings were combined and cooled to 0° C. in an ice bath and then NaBH$_4$(0.659 g, 17.41 mmol) in cold water (10 mL) was added in one portion (gas evolved), then allowed to warm to room temperature and stirred for 2 hours. The reaction mixture was quenched by careful addition of 1M HCl (30 mL) until acidic pH was obtained. The product was extracted into diethyl ether (150 mL). The organic layer was then washed with 2M NaOH (2×100 mL) to removed starting carboxylic acid, then acidified by washing with 1M HCl (100 mL), followed by brine (100 mL), dried over magnesium sulfate, filtered and solvent removed in vacuo. The crude product was purified by chromatography eluting with 0-50% EtOAc/iso-Hexane to afford (6-bromo-2-fluoro-3-methoxy-phenyl)-methanol as a colourless oil, 1.37g, 50% yield.
[MH]$^+$=217/219

1-Bromo-2-chloromethyl-3-fluoro-4-methoxy-benzene

A solution of (6-bromo-2-fluoro-3-methoxy-phenyl)-methanol (500 mg, 2.127 mmol) in anhydrous DCM (4 mL) was treated with triethylamine (415 µL, 2.98 mmol), followed by methanesulfonyl chloride (214 µL, 2.77 mmol). The mixture was allowed to stir at ambient temperature overnight. The reaction mixture was partitioned between DCM (50 mL) and sat. aq. NH$_4$Cl (40 mL). The organic layer was collected and the aqueous layer extracted with further DCM (40 mL). The combined organics were washed with water (40 mL), brine (40 mL), dried (Na$_2$SO$_4$), filtered and concentrated. The crude material was purified by chromatography eluting with a gradient of 0 to 30% EtOAc/iso-Hexane to afford 1-bromo-2-chloromethyl-3-fluoro-4-methoxy-benzene (468 mg, 86% yield) as a white solid.

2-(6-Bromo-2-fluoro-3-methoxy-benzyl)-isoindole-1,3-dione

To a solution of 1-bromo-2-chloromethyl-3-fluoro-4-methoxy-benzene (460 mg, 1.815 mmol) in anhydrous DMF (5 mL) was added potassium phthalimide (403 mg, 2.178 mmol) and the mixture heated at 90° C. overnight. The mixture was diluted with EtOAc (75 mL) and washed with water (3×35 mL), brine (35 mL), dried (Na$_2$SO$_4$), filtered and concentrated to a yellow solid. The crude material was purified by flash chromatography, eluting with a gradient of 0 to 50% EtOAc / iso-Hexane. The desired product 2-(6-bromo-2-fluoro-3-methoxy-benzyl)-isoindole-1,3-dione was isolated as white needles, 372 mg, 56% yield.
[MH]$^+$=364.0/366.0

6-Bromo-2-fluoro-3-methoxy-benzylamine

A suspension of 2-(6-bromo-2-fluoro-3-methoxy-benzyl)-isoindole-1,3-dione (0.368 g, 1.011 mmol) in methanol (7.5 mL) was treated with hydrazine hydrate (0.064 mL, 1.314 mmol) and the reaction mixture heated at reflux for 5 hrs. The crude mixture was loaded directly onto an SCX column (8 g), washed with MeOH and eluted with 1% NH$_3$/MeOH to afford 6-bromo-2-fluoro-3-methoxy-benzylamine (204 mg, 85% yield) as a yellow oil
[MH]$^+$=233.9/235.9

3-Methoxymethyl-1-[4-(2-oxo-2H-pyridin-1-ylmethyl)-benzyl]-1H-pyrazole-4-carboxylic acid 6-bromo-2-fluoro-3-methoxy-benzylamide A 25 mL flask was charged with 3-(methoxymethyl)-1-(4-((2-oxopyridin-1(2H)-yl)methyl)benzyl)-1H-pyrazole-4-carboxylic acid (130 mg, 0.368 mmol), (6-bromo-2-fluoro-3-methoxy-benzylamine (86 mg, 0.368 mmol), HATU (154 mg, 0.405 mmol), anhydrous DCM (3 mL) and anhydrous DMF (0.5 mL). N,N-Disopropylethylamine (160 µL, 0.920 mmol) was added and the mixture allowed to stir at ambient temperature overnight. The reaction was concentrated under vacuum and redissolved in MeOH (4 mL) then purified by SCX, washing with MeOH, eluting with 1% NH$_3$/MeOH. The residue was further purified chromatography eluting with a gradient of 0 to 10% MeOH (containing 0.3% NH$_3$)/DCM to afford 3-methoxymethyl-144-(2-oxo-2H- pyridin-1-ylmethyl)-benzyl]-1H-pyrazole-4-carboxylic acid 6-bromo-2-fluoro-3-methoxy-benzylamide (191 mg, 89% yield) as a white foam.

[MH]⁺=569.2/571.2

N-[(6-Cyano-2-fluoro-3-methoxyphenyl)methyl]-3-(methoxymethyl)-1-({4-[(2-oxopyridin-1-yl)methyl]phenyl}methyl)pyrazole-4-carboxamide To a degassed solution of dicyanozinc (24.13 mg, 0.205 mmol) and 3-methoxymethyl-1-[4-(2-oxo-2H-pyridin-1-yl-methyl)-benzyl]-1H-pyrazole-4-carboxylic acid 6-bromo-2-fluoro-3-methoxy-benzylamide (90 mg, 0.158 mmol) in dimethylacetamide (1.2 mL) was added tetrakis(triphenylphosphine)palladium(0) (18.26 mg, 0.016 mmol) and the mixture heated to 110° C. overnight. The mixture was purified by chromatography eluting with a gradient of 0 to 10% (0.3% NH₃/MeOH) / DCM to give N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide as a pale yellow foam, 21 mg, 25% yield.

[MH]⁺=516.3

¹H NMR (d⁶-DMSO) δ: 3.21 (3H, s), 3.92 (3H, s), 4.47-4.55 (4H, m), 5.06 (2H, s), 5.27 (2H, s), 6.21 (1H, td, J=6.7, 1.4Hz), 6.39 (1H, d, J=9.1Hz), 7.17-7.31 (5H, m), 7.40 (1H, ddd, J=8.9, 6.6, 2.1Hz), 7.67 (1H, dd, J =8.6, 1.5Hz), 7.75 (1H, dd, J=6.8, 2.1Hz), 8.20 (1H, s), 8.40 (1H, t, J=5.2Hz)

N-[(6-Cyano-2-fluoro-3-methoxyphenyl)methyl]-3-(methoxymethyl)-1-({4-[(2-oxopyridin-1-yl)methyl]phenyl}methyl)pyrazole-4-carboxamide (Form 1)

N-[(6-Cyano-2-fluoro-3-methoxyphenyl)methyl]-3-(methoxymethyl)-1-({4-[(2-oxopyridin-1-yl)methyl]phenyl}methyl)pyrazole-4-carboxamide (78 g, crude) was added to IPA (780 mL) and the mixture heated at reflux for 15 min. Additional IPA was added in portions at this temperature over 1 hrs until complete dissolution was observed. A total of 1225 mL of was IPA used. The mixture was allowed to cool for 1 hrs before placing in a cold water bath to reduce the temperature to 20° C. After stirring for 1 hrs the solution was filtered and the solids washed with cold IPA (10° C., 2×200 mL). The solids were suction dried for 2 hrs then in vacuo at 45° C. overnight to give the title compound (58 g, 78% yield from 3-methoxymethyl-1-[4-(2-oxo-2H-pyridin-1-ylmethyl)-benzyl]-1H-pyrazole-4-carboxylic acid 6-bromo-2-fluoro-3-methoxy-benzylamide).

An XRPD diffractogram of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide (Form 1) is shown in FIG. 1.

Peak position table:

| Peak No. | Pos. [°2θ] | Rel. Int. [%] |
|---|---|---|
| 1 | 8.4901 | 8.99 |
| 2 | 9.0102 | 87.95 |
| 3 | 10.1381 | 8.03 |
| 4 | 14.3134 | 77.39 |
| 5 | 15.0582 | 6.5 |
| 6 | 15.4267 | 12.39 |
| 7 | 16.4999 | 9.98 |
| 8 | 18.1335 | 79.47 |
| 9 | 18.2871 | 48.33 |
| 10 | 18.9988 | 20.47 |
| 11 | 19.5778 | 100 |
| 12 | 21.2755 | 46.67 |
| 13 | 22.591 | 4.73 |
| 14 | 23.5478 | 32.59 |
| 15 | 23.9744 | 48.11 |
| 16 | 25.7605 | 11.79 |
| 17 | 27.1429 | 35.56 |
| 18 | 28.4582 | 31.39 |
| 19 | 32.3835 | 7.85 |
| 20 | 33.4322 | 8.17 |
| 21 | 35.5026 | 9.76 |
| 22 | 39.2328 | 6.71 |

Simultaneous Thermal Analysis (STA)

The STA data for Form 1 are shown in FIG. 2.

Differential Scanning Calorimetry (DSC)

The DSC data for Form 1 are shown in FIG. 3.

Microscopy

Microscopy studies were performed on Form 1 using an AxioVert 35M equipped with an AxioCam ERc 5s equipment #1612. The microscope is equipped with four lenses: Zeiss A-Plan 5x/0.12, Zeiss A-Plan 10x/0.25, LD A-Plan 20x/0.30 and Achros TIGMAT 32x/0.40. Data collection and evaluation was performed using Carl Zeiss Zen AxioVision Blue Edition Lite 2011 v1.0.0.0 software. A small amount of sample is loaded on an object glass and carefully spread until a thin layer is obtained.

The images obtained are shown in FIGS. 4(a) and 4(b).

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (Form 2)

A mixture of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (30 mg) in IPA (300 µL) was heated. The resulting supersaturated solution or suspension was filtered into methyl tert-butyl ether (t-BME) (750 µL) at ambient temperature. When solid crystallised, excess solvent was decanted off and the solids were dried by evaporation under nitrogen to afford N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide (Form 2).

An XRPD diffractogram of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (Form 2) is shown in FIG. 5.

Peak position table:

| Peak No. | Pos. [°2θ] | Rel. Int. [%] |
|---|---|---|
| 1 | 7.7034 | 11.2 |
| 2 | 8.3089 | 55.25 |
| 3 | 10.5262 | 66.71 |
| 4 | 11.7257 | 37.49 |
| 5 | 14.0517 | 44.51 |
| 6 | 14.6798 | 23.5 |
| 7 | 15.608 | 52.52 |
| 8 | 16.5881 | 94.72 |
| 9 | 17.4845 | 66.99 |
| 10 | 18.5032 | 48.04 |
| 11 | 18.9247 | 18.45 |
| 12 | 19.6269 | 42.04 |
| 13 | 20.9424 | 63.21 |

-continued

Peak position table:

| Peak No. | Pos. [°2θ] | Rel. Int. [%] |
|---|---|---|
| 14 | 21.7838 | 64.41 |
| 15 | 22.3573 | 29.49 |
| 16 | 23.8415 | 85.13 |
| 17 | 24.7883 | 28.25 |
| 18 | 25.5258 | 51.49 |
| 19 | 26.8795 | 19.14 |
| 20 | 27.3777 | 22.28 |
| 21 | 27.9418 | 100 |
| 22 | 28.4407 | 85.63 |
| 23 | 28.876 | 43.44 |
| 24 | 31.0058 | 32.27 |
| 25 | 32.0679 | 51.16 |
| 26 | 32.7221 | 17.48 |
| 27 | 33.6309 | 14.46 |
| 28 | 36.2689 | 17.76 |
| 29 | 38.7838 | 20.05 |

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (Form 3)

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (19.8 mg) in 90/10 IPA/water (400 µL) was heated to dissolve the solid, filtering if necessary. The resulting solution was cooled by plunging the warm solution into a dry ice/acetone bath. The sample was then transferred into a freezer (at a temperature of approximately −20° C.). The resulting solids were isolated to afford N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (Form 3).

An XRPD diffractogram of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide (Form 3) is shown in FIG. 6.

Peak position table:

| No. | Pos. [°2Th.] | Rel. Int. [%] |
|---|---|---|
| 1 | 6.1849 | 2.12 |
| 2 | 7.2829 | 8 |
| 3 | 8.2935 | 2.46 |
| 4 | 10.1555 | 6.9 |
| 5 | 10.5403 | 3.12 |
| 6 | 12.4185 | 100 |
| 7 | 12.8992 | 21.96 |
| 8 | 13.7105 | 8.2 |
| 9 | 17.6151 | 5.3 |
| 10 | 18.1391 | 13.65 |
| 11 | 18.7515 | 6.55 |
| 12 | 19.4193 | 5.03 |
| 13 | 20.4747 | 6.31 |
| 14 | 21.3389 | 3.01 |
| 15 | 22.139 | 7.56 |
| 16 | 23.9975 | 10.02 |
| 17 | 24.7209 | 6.68 |
| 18 | 25.7964 | 3.52 |
| 19 | 27.6906 | 2.17 |
| 20 | 29.7329 | 2.19 |
| 21 | 30.9964 | 5.32 |
| 22 | 37.577 | 2.46 |

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (Form 4)

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (20.8 mg) in dichloromethane (200 µL) was heated to dissolve the solid, filtering if necessary. The resulting solution was cooled by plunging the warm solution into a dry ice/acetone bath. The sample was then transferred into a freezer (at a temperature of approximately −20° C. The resulting solids were isolated to afford N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (Form 4).

An XRPD diffractogram of N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide (Form 4) is shown in FIG. 7.

Peak position table:

| No. | Pos. [°2Th.] | Rel. Int. [%] |
|---|---|---|
| 1 | 8.9675 | 65.17 |
| 2 | 10.8749 | 16.38 |
| 3 | 13.2706 | 15.34 |
| 4 | 14.3088 | 81.28 |
| 5 | 14.7684 | 52.52 |
| 6 | 14.9571 | 84.14 |
| 7 | 15.3361 | 30.85 |
| 8 | 15.9537 | 32.37 |
| 9 | 17.2585 | 45.82 |
| 10 | 18.1361 | 82.58 |
| 11 | 18.881 | 79.46 |
| 12 | 19.2796 | 78.53 |
| 13 | 19.5731 | 77.97 |
| 14 | 20.1492 | 41.37 |
| 15 | 21.2761 | 43.22 |
| 16 | 23.4839 | 49.54 |
| 17 | 24.0266 | 67.58 |
| 18 | 25.2749 | 52.56 |
| 19 | 26.9997 | 100 |
| 20 | 28.421 | 37.37 |

Alternatively, Form 4 may be prepared using the following method: A mixture of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (29.7 mg) in anisole (450 µL) was heated. The resulting supersaturated solution or suspension was filtered into methyl tert-butyl ether (t-BME) (750 µL) at ambient temperature. When solid crystallised, excess solvent was decanted off and the solids were dried by evaporation under nitrogen to afford N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide (Form 4).

Biological Methods

The ability of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide to inhibit plasma kallikrein may be determined using the following biological assays:

Determination of the $IC_{50}$ for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 25° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

When tested in this assay, N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide showed an $IC_{50}$ (human PKal) of 0.6 nM.

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide was also screened for inhibitory activity against the related enzyme KLK1 using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human KLK1 (Callbiochem) was incubated at 25° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

When tested in this assay, N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide showed an $IC_{50}$ (human KLK1) of >40000 nM.

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide was also screened for inhibitory activity against the related enzyme FXIa using the following biological assay:

Determination of the % Inhibition for FXIa

FXIa inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human FXIa (Enzyme Research Laboratories) was incubated at 25° C. with the fluorogenic substrate Z-Gly-Pro-Arg-AFC and 40 µM of the test compound. Residual enzyme activity (initial rate of reaction) was determined by measuring the change in optical absorbance at 410 nm.

When tested in this assay, N-[(6-cyano-2-fluoro-3-methoxypheyl)methyl]-3-(methoxymethyl)-1-({4-[(2-oxopyridin-1-yl)methyl]phenyl}methyl)pyrazole-4-carboxamide showed a % inhibition @ 40 µM (human FXIa) of 28%.

Pharmacokinetics

A pharmacokinetic study of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide was performed to assess the pharmacokinetics following a single oral dose in male Sprague-Dawley rats. Two rats were given a single po dose of 5 mL/kg of a nominal 2 mg/mL (10 mg/kg) composition of test compound in vehicle. Following dosing, blood samples were collected over a period of 24 hours. Sample times were 5, 15 and 30 minutes then 1, 2, 4, 6, 8 and 12 hours. Following collection, blood samples were centrifuged and the plasma fraction analysed for concentration of test compound by LCMS.

Oral exposure data acquired from this study for N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide is shown below:

| Vehicle | Dose po (mg/kg) | Cmax (ng/mL) | Tmax (min) |
|---|---|---|---|
| 10% DMSO/10% cremophor/80% SWFI | 5.5 | 397 | 30 |
| 10% DMSO/10% cremophor/80% SWFI | 7.8 | 360 | 60 |

The invention claimed is:

1. A crystalline form of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, that is:
   (a) crystalline Form 1, which exhibits at least X-ray powder diffraction peaks (Cu Kα radiation, expressed in degrees 2θ) at 9.0±0.3, 14.3±0.3, 18.1±0.3, 19.6±0.3 and 24.0±0.3; or
   (b) crystalline Form 2, which exhibits at least X-ray powder diffraction peaks (Cu Kα radiation, expressed in degrees 2θ) at 8.3±0.3, 10.5±0.3, 16.6±0.3, 19.6±0.3, and 23.8±0.3; or
   (c) crystalline Form 3, which exhibits at least X-ray powder diffraction peaks (Cu Kα radiation, expressed in degrees 2θ) at 7.3±0.3, 10.2±0.3, 12.4±0.3, 12.9±0.3 and 18.1±0.3; or
   (d) crystalline Form 4, which exhibits at least X-ray powder diffraction peaks (Cu Kα radiation, expressed in degrees 2θ) at 9.0±0.3, 14.3±0.3, 15.0±0.3, 18.1±0.3, and 19.5±0.3.

2. The crystalline form 1 of claim 1 having an X-ray powder diffraction pattern substantially the same as that shown in FIG. 1.

3. The crystalline form 1 of claim 1, which exhibits an endothermic peak in its DSC thermograph at 149±3° C.

4. The crystalline form 1 of claim 1 having a DSC thermograph substantially the same as that shown in FIG. 3.

5. A crystalline form 1 of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, which exhibits an endothermic peak in its DSC thermograph at 149±3° C.

6. The crystalline form 1 of claim 5 having a DSC thermograph substantially the same as that shown in FIG. 3.

7. The crystalline form 2 of claim 1, which exhibits at least X ray powder diffraction peaks (Cu Kα radiation, expressed in degrees 2θ) at 8.3±0.3, 10.5±0.3, 16.6±0.3, 19.6±0.3 and 23.8±0.3.

8. The crystalline form 2 of claim 7 having an X-ray powder diffraction pattern substantially the same as that shown in FIG. 5.

9. The crystalline form 3 of claim 1, which exhibits at least X ray powder diffraction peaks (Cu Kα radiation, expressed in degrees 2θ) at 7.3±0.3, 10.2±0.3, 12.4±0.3, 12.9±0.3 and 18.1±0.3.

10. The crystalline form 3 of claim 9 having an X-ray powder diffraction pattern substantially the same as that shown in FIG. 6.

11. The crystalline form 4 of claim 1, which exhibits at least X ray powder diffraction peaks (Cu Kα radiation, expressed in degrees 2θ) at 9.0±0.3, 14.3±0.3, 15.0±0.3, 18.1±0.3 and 19.5±0.3.

12. The crystalline form 4 of claim 11 having an X-ray powder diffraction pattern substantially the same as that shown in FIG. 7.

13. A pharmaceutical composition comprising a crystalline form of claim 1 and a pharmaceutically acceptable adjuvant, diluent or carrier.

14. A method for treating a disease or condition mediated by plasma kallikrein, comprising administering a crystalline form of claim 1 to a patient having said disease or condition.

15. The method of claim 14, wherein the disease or condition mediated by plasma kallikrein is impaired visual acuity, diabetic retinopathy, retinal vascular permeability associated with diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, or bleeding from post-operative surgery.

16. The method of claim 14, wherein the disease or condition mediated by plasma kallikrein is retinal vascular permeability associated with diabetic retinopathy, diabetic macular edema, or hereditary angioedema.

17. The method of claim 16, wherein the disease or condition mediated by plasma kallikrein is retinal vascular permeability associated with diabetic retinopathy, or diabetic macular edema.

18. The method of claim 16, wherein the disease or condition mediated by plasma kallikrein is hereditary angioedema.

19. The method of claim 16, wherein the disease or condition mediated by plasma kallikrein is diabetic macular edema.

20. The method of claim 14, wherein the disease or condition mediated by plasma kallikrein is retinal vein occlusion.

21. The method of claim 17 wherein said crystalline form is administered in a form suitable for injection into the ocular region of the patient.

22. The method of claim 14, wherein said crystalline form is in a form suitable for oral administration.

23. The method of claim 14, wherein the crystalline form is administered orally.

24. A process for preparing the crystalline form 1 of claim 1, comprising crystallising said crystalline form 1 from a mixture of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide and isopropyl alcohol.

25. The process of claim 24, wherein said mixture is heated to a temperature of approximately 60-85° C.

26. The process of claim 25, wherein, after heating, said mixture is cooled to a temperature of approximately 0-40° C.

27. A process for preparing the crystalline form 2 of claim 1, comprising crystallising said crystalline form from a mixture of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, isopropyl alcohol (IPA) and methyl tert-butyl ether.

28. The process of claim 27, wherein after adding the N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide to IPA, the combined mixture is added to methyl tert-butyl ether.

29. A process for preparing the crystalline form 3 of claim 1, comprising crystallising said crystalline form from a mixture of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide, isopropyl alcohol (IPA), and water.

30. The process of claim 29, wherein after adding the N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide to IPA and water, the combined mixture is heated before cooling to a temperature of about 0 to −80° C.

31. A process for preparing the crystalline form 4 of claim 1, comprising crystallising said crystalline form from a mixture of N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide and (i) dichloromethane or (ii) anisole and methyl tert-butyl ether.

32. The process of claim 31, wherein the crystallizing is performed with dichloromethane.

33. The process of claim 32, wherein after adding the N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide to dichloromethane, the combined mixture is heated before cooling to a temperature of about 0 to −80° C.

34. The process of claim 31, wherein the crystallizing is performed with anisole and methyl tert-butyl ether.

35. The process of claim 34, wherein after adding the N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide to anisole, the combined mixture is added to methyl tert-butyl ether.

36. The crystalline Form 1 of claim 1, which exhibits at least X-ray powder diffraction peaks (Cu Kα radiation, expressed in degrees 2θ) at 9.0±0.3, 14.3±0.3, 18.1±0.3, 19.6 ±0.3, and 24.0±0.3.

37. The method of claim 21, wherein said solid form is administered in a form suitable for intra-vitreal injection.

* * * * *